US012616662B2

(12) United States Patent
Peer et al.

(10) Patent No.: US 12,616,662 B2
(45) Date of Patent: May 5, 2026

(54) LIPID PARTICLES FOR NUCLEIC ACID DELIVERY AND CLINICAL APPLICATIONS OF SAME

(71) Applicant: Ramot at Tel-Aviv University Ltd., Tel-Aviv (IL)

(72) Inventors: Dan Peer, Tel-Aviv (IL); Daniel Rosenblum, Tel-Aviv (IL); Anna Gutkin, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 756 days.

(21) Appl. No.: 17/988,824

(22) Filed: Nov. 17, 2022

(65) Prior Publication Data

US 2023/0201127 A1 Jun. 29, 2023

Related U.S. Application Data

(63) Continuation of application No. PCT/IL2021/050571, filed on May 19, 2021.

(60) Provisional application No. 63/026,785, filed on May 19, 2020.

(51) Int. Cl.

| | |
|---|---|
| ***A61K 9/51*** | (2006.01) |
| ***A61K 31/7088*** | (2006.01) |
| ***A61K 38/46*** | (2006.01) |
| ***A61P 35/00*** | (2006.01) |

(52) U.S. Cl.

CPC ........ *A61K 9/5123* (2013.01); *A61K 31/7088* (2013.01); *A61K 38/465* (2013.01); *A61P 35/00* (2018.01)

(58) Field of Classification Search

None

See application file for complete search history.

(56) References Cited

U.S. PATENT DOCUMENTS

| | | | | |
|---|---|---|---|---|
| 10,557,125 | B2 * | 2/2020 | Dumas | C12N 15/09 |
| 2021/0299228 | A1 * | 9/2021 | Ruan | C12N 9/22 |

FOREIGN PATENT DOCUMENTS

| | | |
|---|---|---|
| JP | 2020-512272 | 4/2020 |
| WO | WO 2016/189532 | 12/2016 |
| WO | WO 2018/015881 | 1/2018 |
| WO | WO 2018/087753 | 5/2018 |
| WO | WO 2020/051220 | 3/2020 |
| WO | WO 2020/051223 | 3/2020 |
| WO | WO 2020/089342 | 5/2020 |
| WO | WO 2021/234694 | 11/2021 |

OTHER PUBLICATIONS

Glass, et al. (2018) "Engineering the Delivery System for CRISPR/Based Genome Editing", Trends in Biotechnology, 36(2): 173-85. (Year: 2018).*

Zaghloul, et al. (2010) "Functional analyses of variants reveal a significant role for dominant negative and common alleles in oligogenic Bardet-Biedel syndrome", Proceedings of the National Academy of Science, USA, 107(23): 10602-07. (Year: 2010).*

D'Aloia, et al. (2018) "CAR-T cells: the long and winding road to solid tumors", Cell Death and Disease, 9: 282, 12 pages as printed. (Year: 2018).*

Katz (2013) "Gene Therapy Delivery Systems for Enhancing Viral and Nonviral Vectors for Cardiac Diseases: Current Concepts and Future Applications", Human Gene Therapy, 24(11): 914-27. (Year: 2013).*

Cholewa, et al. (2013) "The role of polo-like kinase 1 in carcinogenesis: cause or consequence?", Cancer Research, 73(23): 6848-55. (Year: 2013).*

Whyte, et al. (2012) "Enzyme-Replacement Therapy in Life-Threatening Hypophosphatasia", The New England Journal of Medicine , 366(10): 904-13. (Year: 2012).*

Author unknown (2025) "D-Lin-MC3-DMA A Critical Ionizable Lipid for Lipid Nanoparticles", No Volume, No Issue, 4 pages as printed. (Year: 2025).*

Supplementary European Search Report and the European Search Opinion Dated Mar. 25, 2024 From the European Patent Office Re. Application No. 21809082.7. (19 Pages).

Kedmi et al. "A Modular Platform for Targeted RNAi Therapeutics", Nature Nanotechnology, 13(3): 214-219, XP093140904, Jan. 29, 2018.

Oyane et al. "Fabrication of DNA-Lipid-Apatite Composite Layer for Efficient and Area-Specific Gene Transfer", Journal of Materials Science: Materials in Medicine, 23(4): 1011-1019, XP035038139, Feb. 25, 2012.

Takahashi et al. "Synthesis of Novel Cationic Lipids Having Polyamidoamine Dendrons and Their Transfection Activity", Bioconjugate Chemistry, 14(4): 764-773, XP001170956, Jul. 1, 2003.

Zhang et al. "Lipid Nanoparticle-Mediated Efficient Delivery of CRISPR/Cas9 for Tumor Therapy", NPG Asia Materials, 9(10): 1-8, XP055624557, Oct. 1, 2017.

International Preliminary Report on Patentability Dated Dec. 1, 2022 From the International Bureau of WIPO Re. Application No. PCT/IL2021/050571. (9 Pages).

International Search Report and the Written Opinion Dated Aug. 30, 2021 From the International Searching Authority Re. Application No. PCT/IL2021/050571. (16 Pages).

Oberli et al. "Lipid Nanoparticle Assisted mRNA Delivery for Potent Cancer Immunotherapy", Nano Letters, 17(3): 1326-1335, Published Online Nov. 23, 2016.

Ramishetti et al. "A Combinatorial Library of Lipid Nanoparticles for RNA Delivery to Leukocytes", Advanced Materials, 32(12): 1906128-1-1906128-8, Published Online Jan. 30, 2020.

(Continued)

*Primary Examiner* — Robert M Kelly

(57) ABSTRACT

Lipid particles for nucleic acid delivery and clinical applications of same are provided. Accordingly there is provided a lipid particle comprising a cationic lipid encapsulating a nucleic acid sequence, wherein said nucleic acid sequence encodes a protein having a length of at least 500 amino acids, the cationic lipid being represented by Formula I, as defined in the specification.

Figures 1A, 1B, 1C:
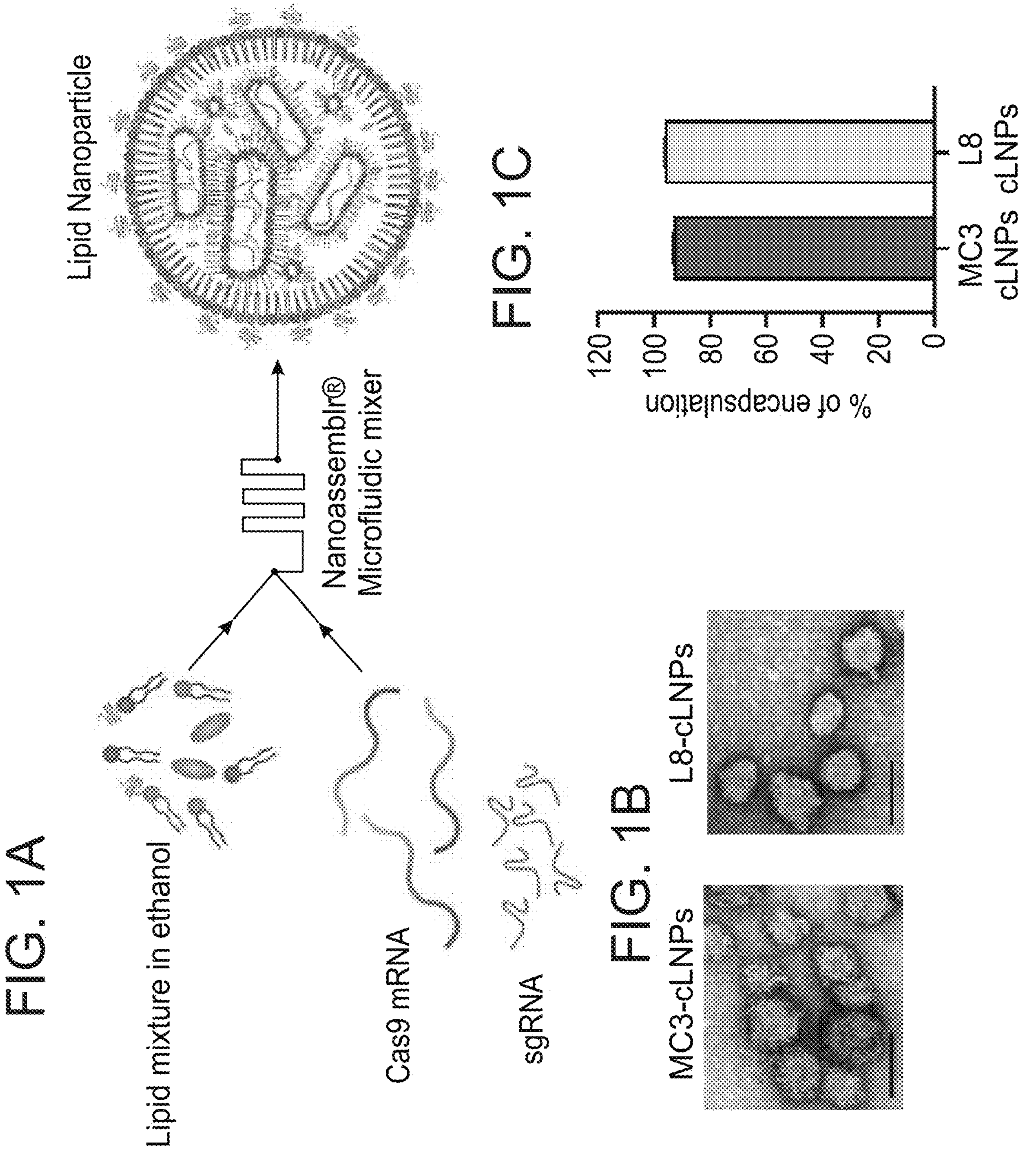

12 Claims, 17 Drawing Sheets
(17 of 17 Drawing Sheet(s) Filed in Color)

Specification includes a Sequence Listing.

(56) References Cited

OTHER PUBLICATIONS

Tam et al. "Pieter Cullis' Quest for a Lipid-Based, Fusogenic Delivery System for Nucleic Acid Therapeutics: Success With SiRNA So What About mRNA?", Journal of Drug Targeting, 24(9): 774-779, Published Online Sep. 2, 2016.
Notice of Reason(s) for Rejection Dated May 13, 2025 From the Japan Patent Office Re. Application No. 2022-570625 and Its Translation Into English. (19 Pages).
Finn et al. "A Single Administration of CRISPR/Cas9 Lipid Nanoparticles Achieves Robust and Persistent in Vivo Genome Editing", Cell Reports, 22: 2227-2235, Feb. 27, 2018.

* cited by examiner

Live cells (% of mock)
120
100
80
60
40
20
0
Mock 0.1 0.25 0.5 1
Concentration (μg/ml)

Mock
sgGFP-cLNPs
sgPLK1-cLNPs
Count
300
200
100
0
G1\G0
67.4
G2\M
19.8
70.0
29.9
10.7
79.7
2.0M
4.0M
6.0M
DAPI Live cells (% of mock)
****
Mock
sgGFP cLNPs
sgPLK1 cLNPs DAPI
Annexin V- APC
0.56
0.11
99.1
0.25
1.46
0.95
96.5
1.12
9.18
19.4
36.3
35.2

LIPID PARTICLES FOR NUCLEIC ACID DELIVERY AND CLINICAL APPLICATIONS OF SAME

RELATED APPLICATIONS

This application is a Continuation (CON) of PCT Patent Application No. PCT/IL2021/050571 having International filing date of May 19, 2021, which claims the benefit of priority under 35 USC § 119(e) of U.S. Provisional Patent Application No. 63/026,785 filed on May 19, 2020. The contents of the above applications are all incorporated by reference as if fully set forth herein in their entirety.

SEQUENCE LISTING STATEMENT

The XML file, entitled 94609SequenceListing.xml, created on Nov. 17, 2022, comprising 11,460 bytes, submitted concurrently with the filing of this application is incorporated herein by reference.

FIELD AND BACKGROUND OF THE INVENTION

The present invention, in some embodiments thereof, relates to lipid particles for nucleic acid delivery and clinical applications of same.

Polynucleotide- or protein-based therapies are limited by the difficult cellular internalization of these macromolecules. Several delivery systems have been developed and proposed to improve cell permeability of these molecular therapies. Examples of these systems range from cell electroporation to viral delivery, the use of lipid particles (e.g. liposomes, lipid nanoparticles), inorganic compounds (cationic polymers, nanotubes, nanoparticles) and cell-penetrating peptides (CPPs).

Genome editing is a powerful tool that can be used to induce targeted mutagenesis, deletions or insertions of cellular DNA sequences, and facilitate recombination at a predetermined genetic sequences within a genome; and has numerous therapeutic and biotechnological applications. Current genome editing agents include, for example, meganucleases, engineered zinc finger nucleases (ZFNs), transcription activator-like effector nucleases (TALENs) and CRISPR/Cas system.

However, delivering functional genome editing agents to a cell can be problematic. For example, due to the large size of the CRISPR/Cas system Cas9 nuclease (160 kDa, 4300b), its encapsulation, cell delivery and translation using both viral and non-viral delivery systems remains a challenge. Most in-vivo studies of gene editing have relied on adeno-associated virus (AAV) to deliver CRISPR/Cas components locally or to the liver. Nevertheless, AAV applications are limited by the virus small carrying capacity, immune responses and current lack of targeting [e.g. Senís, E. et al. (2014). Biotechnology Journal 9, 1402-1412]. Lipid nanoparticles (LNPs) are the only clinically approved non-viral delivery system for nucleic acids. These LNPs, based on ionizable lipids, are gaining much attention in the field of RNA therapeutics. However, LNPs formulations that were optimized for siRNA do not efficiently deliver large nucleic acids sequences that should be translated into functional proteins (e.g., mRNAs, plasmids) [see e.g. Tam, Y. K., et al. (2016) Journal of Drug Targeting 24, 774-779, Oberli, M. A. et al. (2017) Nano Letters 17, 1326-1335].

Additional Background art includes:

Ramishetti S. et al. (2020) Adv Mater. January 30:e1906128; and

International Patent Application Publication Nos. WO2016/189532, WO2018/015881 and WO2018/087753.

SUMMARY OF THE INVENTION

According to an aspect of some embodiments of the present invention there is provided a lipid particle comprising a cationic lipid encapsulating a nucleic acid sequence, wherein the nucleic acid sequence encodes a protein having a length of at least 500 amino acids, the cationic lipid being represented by Formula I:

Formula I

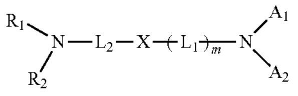

wherein:

m is 0 or 1

A1 and A2 are each independently a saturated or unsaturated linear, non-branched, alkylene chain, of at least 8 carbon atoms in length;

L1 is a first linking group which an alkylene of 1 to 4 carbon atoms in length;

X is —O—C(═O)— or —NH—C(═O);

L2 is a second linking group which is an alkylene of 1 to 4 carbon atoms in length; and R1 and R2 are each independently hydrogen, alkyl or cycloalkyl, or, alternatively, R1 and R2 form together with the nitrogen to which they are attached a heteroalicyclic ring, provided that when X is —O—C(═O)—, m is 1.

According to an aspect of some embodiments of the present invention there is provided a method of preparing a lipid particle for delivery of a nucleic acid sequence, the method comprising encapsulating a nucleic acid sequence in a lipid particle comprising a cationic lipid represented by Formula I:

Formula I

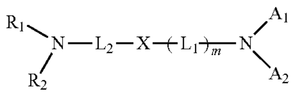

wherein:

m is 0 or 1

A1 and A2 are each independently a saturated or unsaturated linear, non-branched, alkylene chain, of at least 8 carbon atoms in length;

L1 is a first linking group which an alkylene of 1 to 4 carbon atoms in length;

X is —O—C(═O)— or —NH—C(═O);

L2 is a second linking group which is an alkylene of 1 to 4 carbon atoms in length; and R1 and R2 are each independently hydrogen, alkyl or cycloalkyl, or, alternatively, R1 and R2 form together with the nitrogen to which they are attached a heteroalicyclic ring, provided that when X is —O—C(═O)—, m is 1, wherein the nucleic acid sequence encodes a protein having a length of at least 500 amino acids.

According to some embodiments of the invention, the lipid particle comprises a targeting moiety.

According to some embodiments of the invention, the method comprising attaching to the lipid particle a targeting moiety.

According to some embodiments of the invention, the nucleic acid sequence comprises a ribosome binding site sequence, a start codon and an in-frame stop codon.

According to some embodiments of the invention, the nucleic acid sequence is an mRNA.

According to some embodiments of the invention, the protein has a length of at least 1000 amino acids.

According to some embodiments of the invention, the protein is an enzyme.

According to some embodiments of the invention, the enzyme is a genome editing endonuclease.

According to some embodiments of the invention, the genome editing endonuclease is CRISPR-associated endonuclease According to some embodiments of the invention, the CRISPR-associated endonuclease is Cas9.

According to some embodiments of the invention, the nucleic acid sequence comprises SEQ ID NO: 4.

According to some embodiments of the invention, the lipid particle further encapsulates a nucleic acid sequence guiding the genome editing endonuclease to a gene of interest.

According to some embodiments of the invention, the method comprising encapsulating in the lipid particle a nucleic acid sequence guiding the genome editing endonuclease to a gene of interest.

According to some embodiments of the invention, the nucleic acid sequence guiding the genome editing endonuclease to the gene of interest is a CRISPR system gRNA.

According to some embodiments of the invention, the gene of interest is selected from the group consisting of PLK1, Cyclin D1, Sox11, STAT3, CCR5, HIV gene, T-Bet, NIK, CKAP5, LRG5, CA9, HPV E6 and HPV E7.

According to some embodiments of the invention, the particle is a nanoparticle having a size of 30-150 nm.

According to an aspect of some embodiments of the present invention there is provided a method of producing a heterologous protein of interest, the method comprising contacting the cell with the lipid particle, thereby producing the heterologous protein of interest.

According to some embodiments of the invention, the method comprising recovering the protein of interest from the cell following the contacting.

According to an aspect of some embodiments of the present invention there is provided a method of producing a genetic variation in a cell, the method comprising contacting the cell with the lipid particle, thereby producing the genetic variation in the cell.

According to some embodiments of the invention, the method further comprising administering the cell following the contacting to a subject having a disease in need thereof.

According to an aspect of some embodiments of the present invention there is provided a method of treating a disease that can benefit from exogenous expression of a protein in a cell of a subject, the method comprising administering to the subject a therapeutically effective amount of the lipid particle, thereby treating the disease in the subject.

According to an aspect of some embodiments of the present invention there is provided the lipid particle, for use in treating a disease that can benefit from exogenous expression of the protein in a cell of a subject.

According to an aspect of some embodiments of the present invention there is provided a method of treating a disease that can benefit from producing a genetic variation in a cell of a subject, the method comprising administering to the subject a therapeutically effective amount of the lipid particle, thereby treating the disease in the subject.

According to an aspect of some embodiments of the present invention there is provided the lipid particle, for use in treating a disease that can benefit from producing a genetic variation in a cell of a subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 1D:
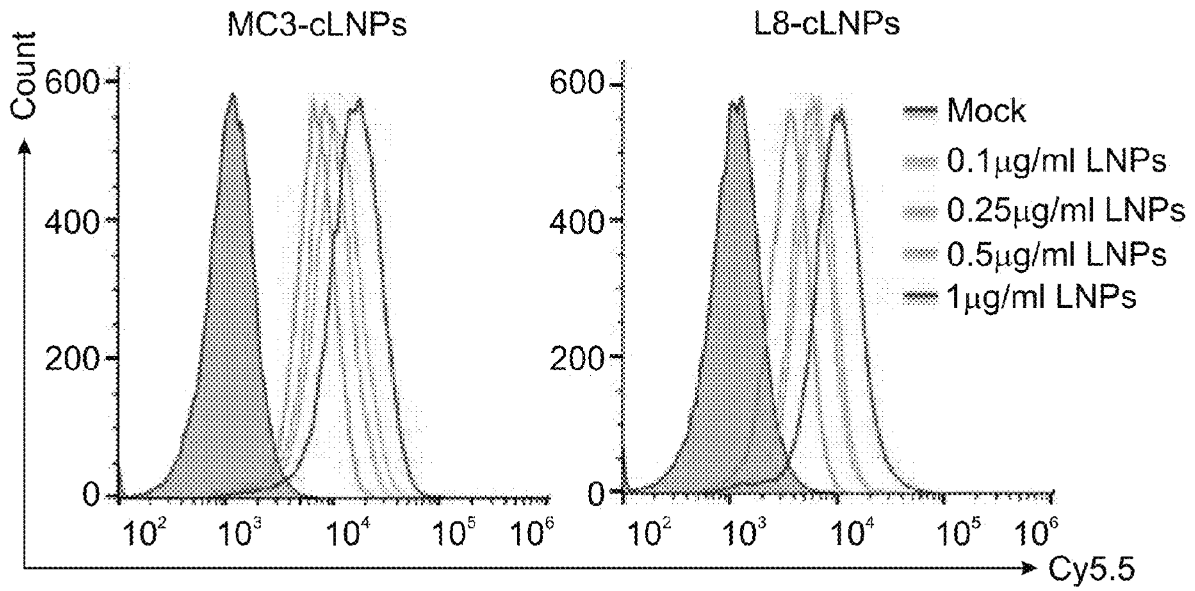
Figure 1E:
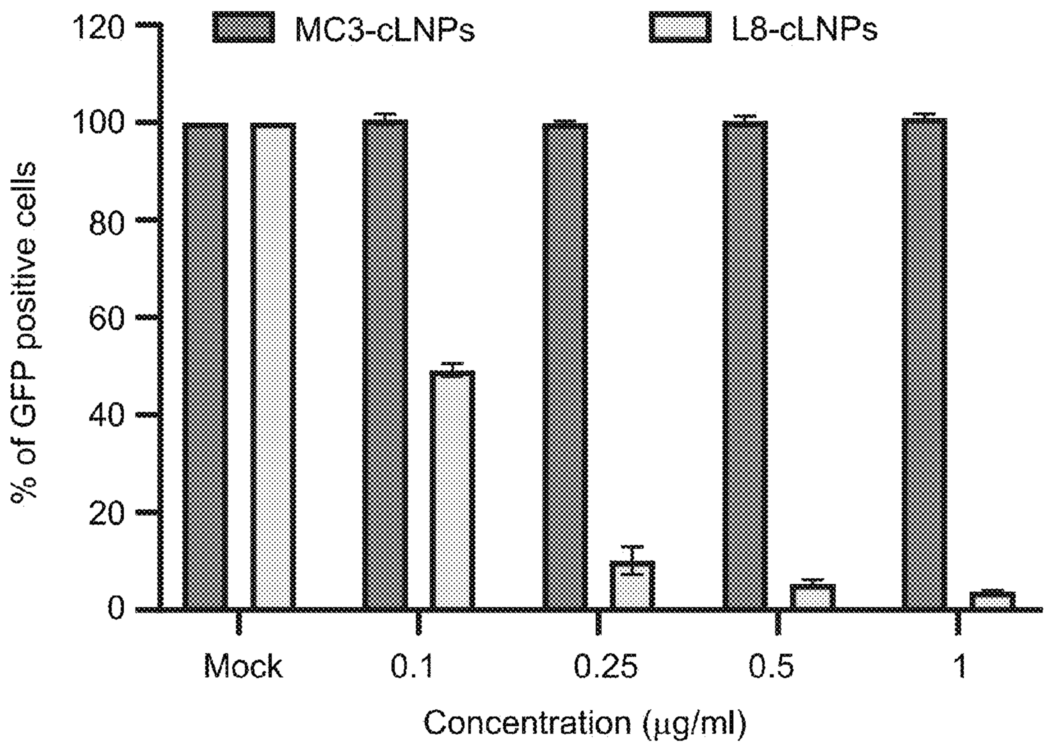
Figure 1F:
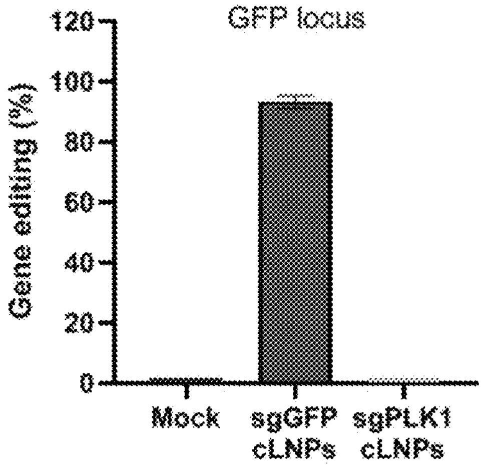
Figure 1G:
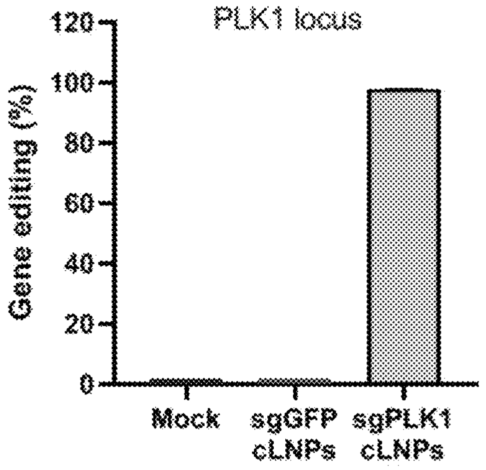
Figure 1H:
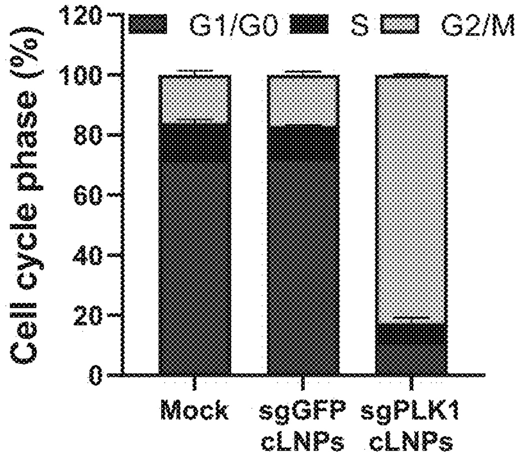
Figure 1I:
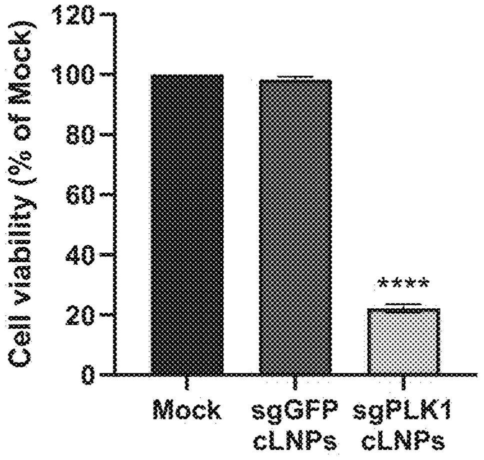

In the drawings:

FIGS. 1A, 1B, 1C, 1D, 1E, 1F, 1G, 1H and 1I demonstrate design, construction and activity of lipid nanoparticles encapsulating the Cas9 mRNA and sgRNA, referred to herein as CRISPR LNPs or cLNPs. FIG. 1A shows a schematic representation of cLNPs preparation. A microfluidic based mixing of lipids to construct cLNPs encapsulating Cas9 mRNA and sgRNA. FIG. 1B shows representative transmission electron microscopy (TEM) images of Dlin-MC3-DMA(MC3)-based (Left) and L8-based (right) cLNPs. Scale bars are 100 nm. FIG. 1C demonstrates encapsulation efficiency as measured using a RiboGreen assay. FIG. 1D demonstrates uptake of MC3-based or L8-based cLNPs by HEK293 cells. Cells were transfected with 0.1-1 μg/ml Cy5.5 labeled cLNPs and analyzed by flow cytometry. Results are presented as the geometric mean of Cy5.5 fluorescence. FIG. 1E demonstrates GFP disruption assay. HEK293 expressing GFP (HEK/GFP) cells were transfected with MC3-based or L8-based cLNPs encapsulating Cas9 mRNA and GFP sgRNA and the % of GFP positive cells was analyzed 72 hours post transfection by flow cytometry. FIGS. 1F-G demonstrate % of gene editing events in the GFP and PLK1 (FIG. 1G) loci, in HEK/GFP cells following transfection with L8-based cLNPs encapsulating Cas9 mRNA and GFP sgRNA (sgGFP cLNPs) or PLK1 sgRNA (sgPLK1 cLNPs), as determined by next generation sequencing analysis. FIG. 1H demonstrates cell cycle analysis of HEK293 cells, 48 hours post treatment with Mock, sgGFP cLNPs or sgPLK1 cLNPs (0.5 μg/ml), as determined by flow cytometry. FIG. 1I demonstrates cell viability of HEK293 cells 96 hours post treatment with Mock, sgGFP cLNPs or sgPLK1 cLNPs (0.5 μg/ml), as determined by XTT assay. Results are presented as the % of Mock treated cells. In FIGS. 1C and 1E-H, data is shown as the mean of ≥three independent experiments, one-way ANOVA with Tukey multiple comparison test was used to assess the significance. In FIG. 1D, data is a representative of three independent experiments.

Figures 2A, 2B, 2C, 2D, 2E, 2F:
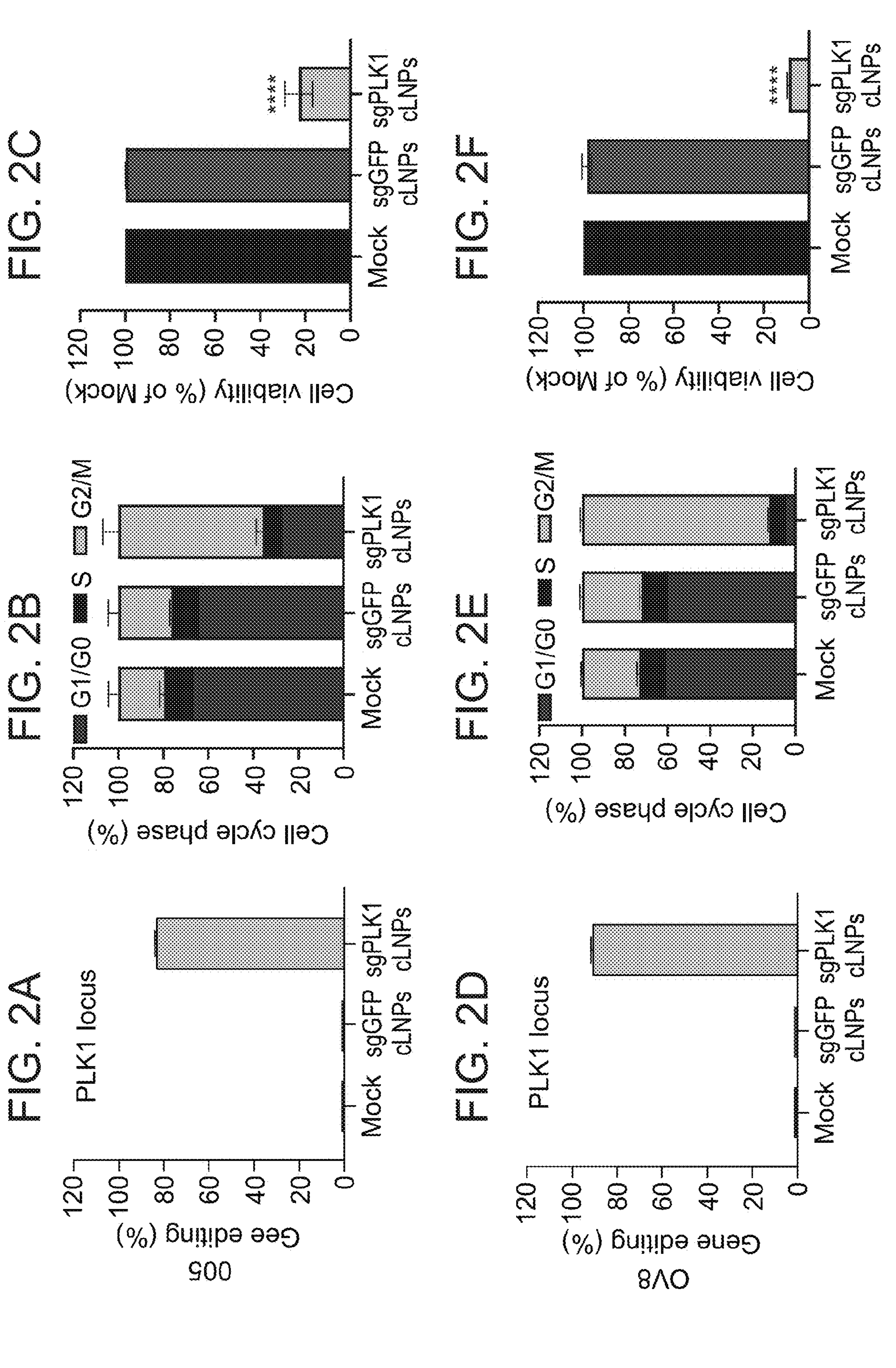

FIGS. 2A, 2B, 2C, 2D, 2E and 2F demonstrate in-vitro genome editing in the murine glioblastoma cell line 005 and the human ovarian cancer cell line OV8 following transfection with L8-based sgGFP cLNPs or sgPLK1 cLNPs. FIGS. 2A and 2D demonstrate % of gene editing events in the GFP and PLK1 loci in 005 (FIG. 2A) and OV8 (FIG. 2D) treatment with the indicated cLNPs or Mock control, as determined by next generation sequencing analysis. FIGS. 2B and 2E demonstrate cell cycle analysis of 005 (FIG. 2B) and OV8 (FIG. 2E) cells 48 hours post treatment with the indicated cLNPs or Mock control (005-0.5 μg/ml, OV8-1 μg/ml), as determined by flow cytometry. FIGS. 2C and 2F demonstrate cell viability of 005 (FIG. 2C) and OV8 (FIG. 2F) cells 96 hours post treatment with the indicated cLNPs or Mock control (005-0.5 μg/ml, OV8—1 μg/ml), as determined by XTT assay. Results are presented as the % of mock treated cells. Data is shows as the mean of ≥three independent experiments, one-way ANOVA with Tukey multiple comparison test was used to assess the significance.

Figure 3A:
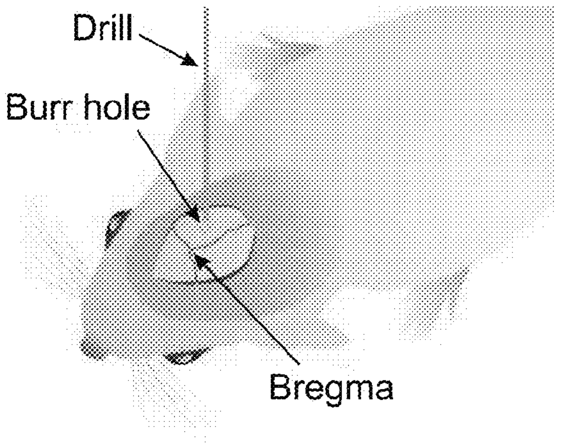
Figure 3B:
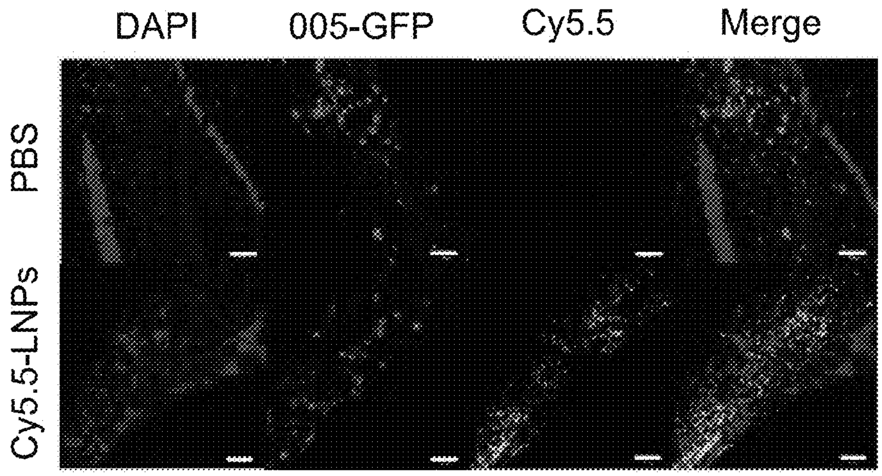
Figure 3C:
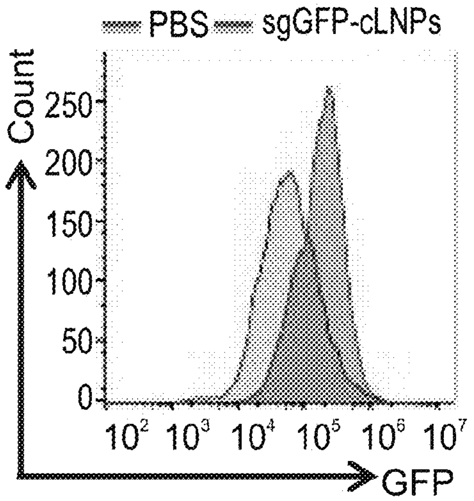
Figure 3D:
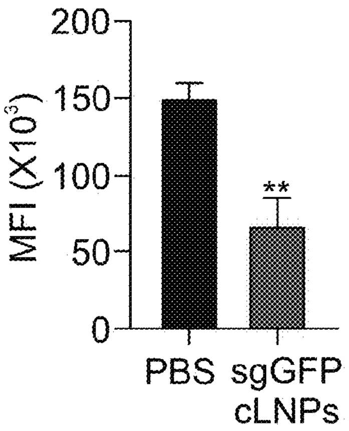
Figure 3E:
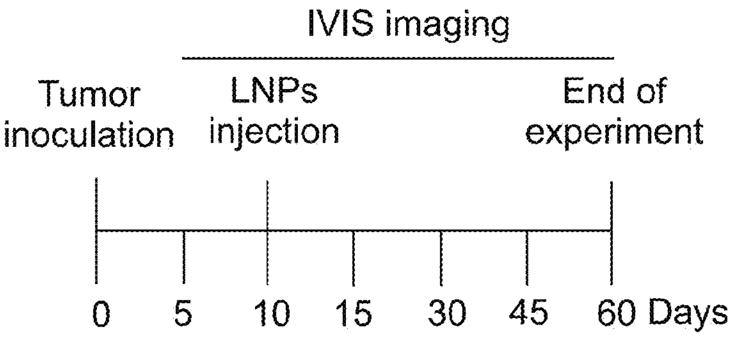
Figure 3F:
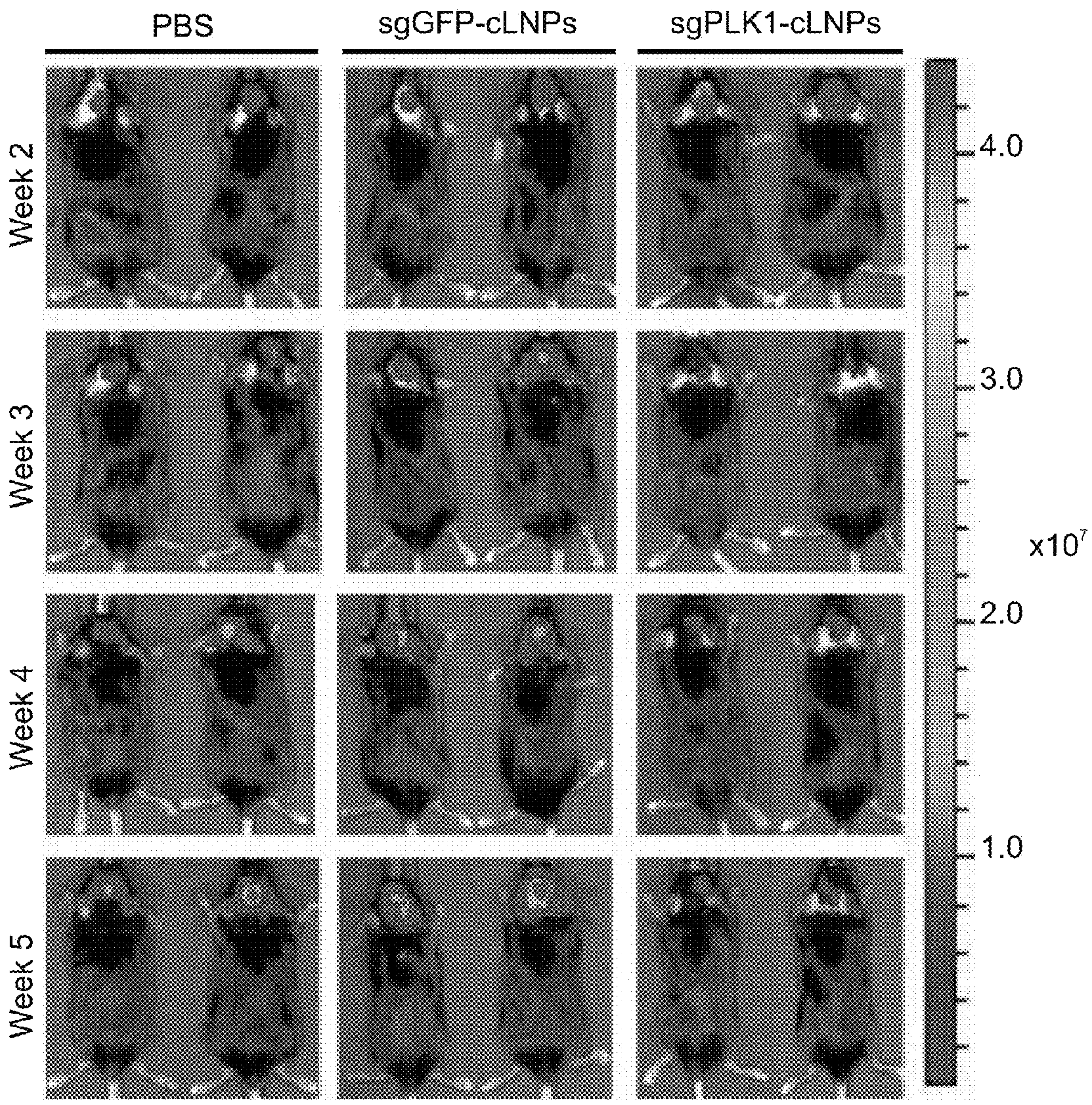
Figure 3G:
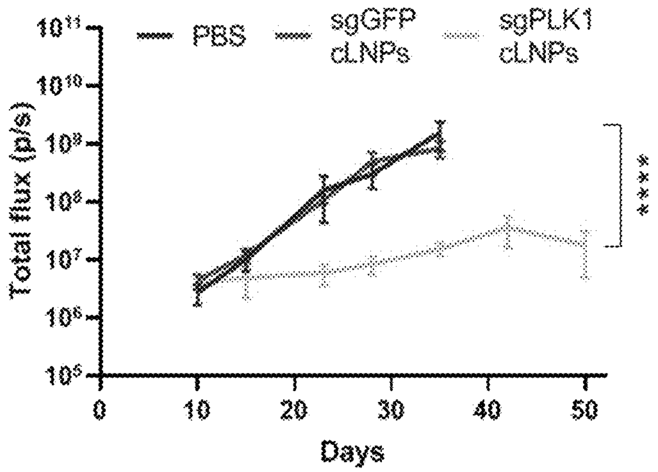
Figure 3H:
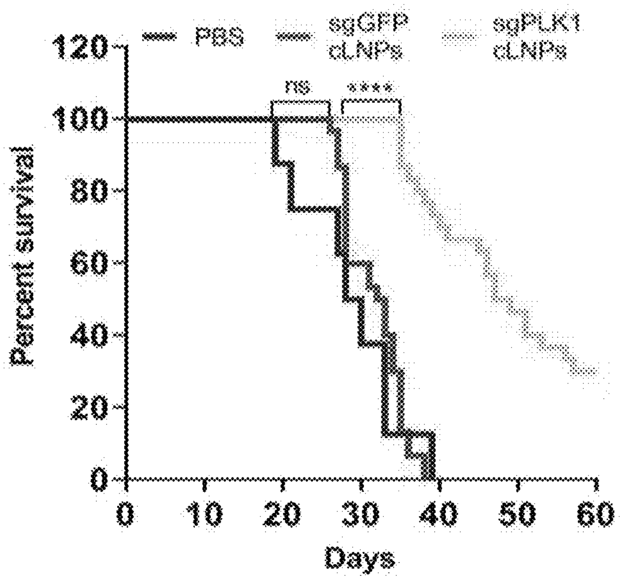

FIGS. 3A, 3B, 3C, 3D, 3E, 3F, 3G and 3H demonstrate therapeutic in-vivo genome editing in 005 GBM bearing mice following injection with L8-based cLNPs. FIG. 3A shows a schematic representation of intra cranial injection to the mouse hippocampus. FIG. 3B demonstrates cLNPs dispersion through the tumor lesion upon intra-cranial injection. Cy5.5 labeled cLNPs were injected intracranially to the tumor bed of 005 GBM bearing mice. 6 hours post injection mice were euthanized and brain section were analyzed by confocal microscopy. Blue-DAPI, green-005 GFP, and yellow Cy5.5 cLNPs. Scale bars 50 μm. FIG. 3C-D demonstrate in-vivo GFP disruption in 005 GBM bearing mice following injection of 0.05 mpk sgGFP-cLNPs to the tumor bed. 7 days post injection brains were processed to single cell suspensions and the reduction in GFP was analyzed by flow cytometry. FIG. 3C shows a representative flow cytometry histogram. FIG. 3D shows mean fluorescent intensity+SD of three independent experiments. P<0.005. FIG. 3E is a schematic representation of the experimental design for evaluating tumor growth. 005 cells were injected intracranially to the hippocampus. 10 days post tumor inoculation 0.05 mpk of sgGFP-cLNPs, sgPLK1-cLNPs or PBS were injected to the tumor bed using an automatic syringe pump at a rate of 0.3 μl/min. Tumor growth was monitored using bioluminescence of 005-GFP-Luc cells using IVIS spectrum CT in-vivo imaging system. FIGS. 3F-G demonstrate tumor growth inhibition by a single dose of sgPLK-cLNPs. FIG. 3F shows representative bioluminescence images of treated mice. FIG. 3G shows tumor growth curve quantification using bioluminescence in-vivo Imaging. Data is presented in Total flux (p/s)±SEM, n=15 animals per treatment group, n=8 animals in the PBS group, p<0.0001. One-way ANOVA was used to assess the significance at day 41. FIG. 3H shows Kaplan-Meier survival curves of treated mice. n=30 animals per treatment group, n=8 animal in the PBS group. **P<0.0001. Log-rank (Mantel-Cox) test was used for curve comparison.

Figure 4A:
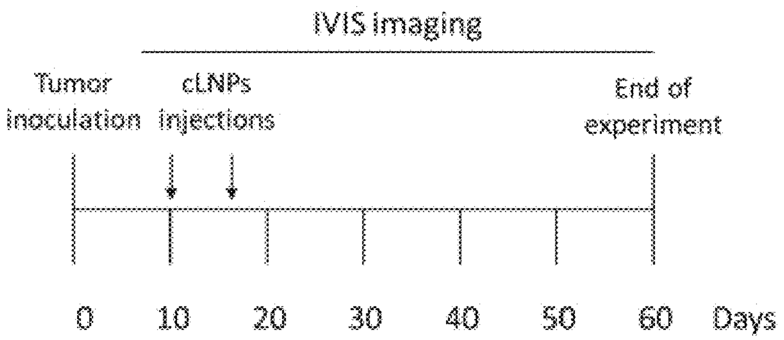
Figure 4B:
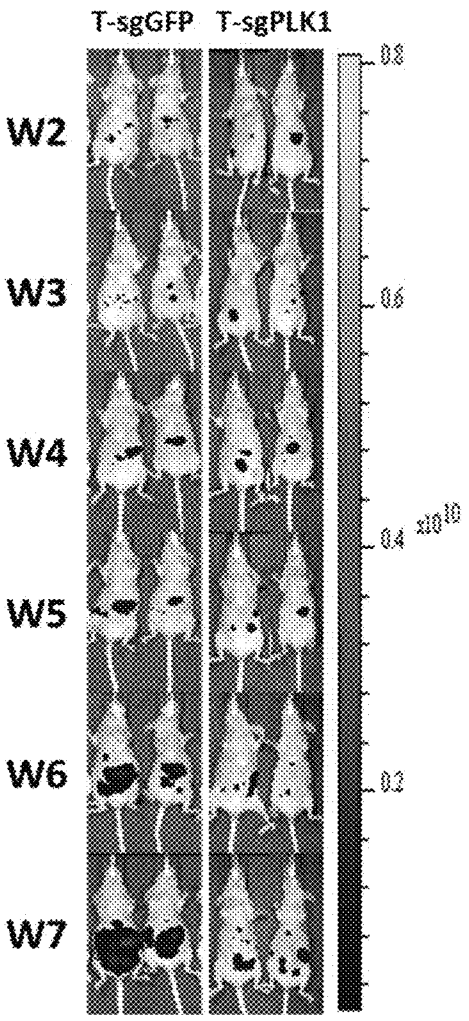
Figure 4C:
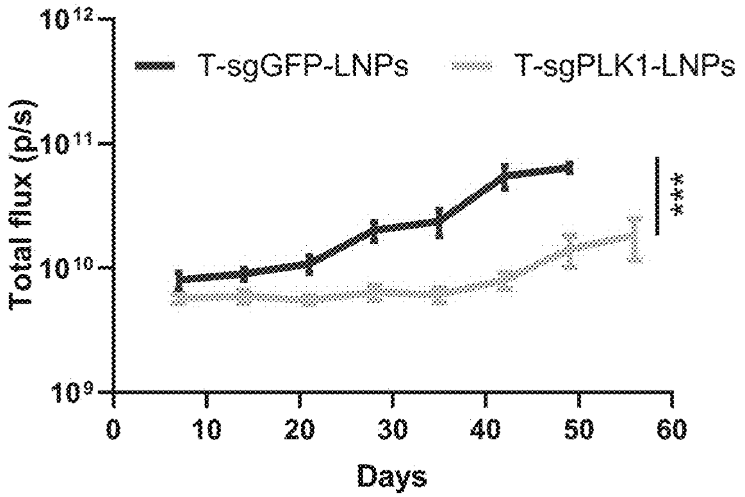
Figure 4D:
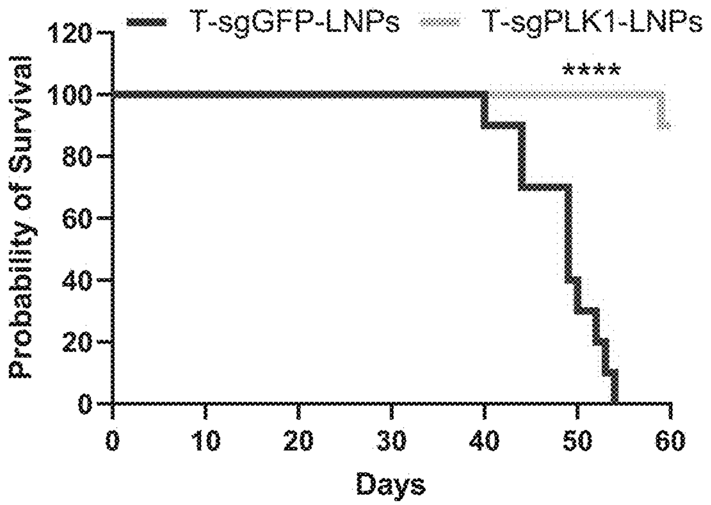

FIGS. 4A, 4B, 4C and 4D demonstrate therapeutic in-vivo genome editing in OV8 bearing mice following injection with anti-hEGFR-targeted L8-based sgPLK1 cLNPs. FIG. 4A is a schematic representation of the experimental design. OV8-mCherry cells were injected intraperitoneally (i.p) to eight weeks old athymic nu/nu mice. Ten and seventeen days post tumor inoculation 0.75 mpk of either sgPLK1 cLNPs or sgGFP cLNPs conjugated to anti-hEGFR (T-sgPLK1 or T-sgGFP, respectively) were injected i.p. Tumor growth was monitored using mCherry fluorescence of OV8-mCherry cells using IVIS spectrum CT in vivo imaging system. FIGS. 4B-C demonstrate inhibition of tumor growth by T-sgPLK1 cLNPs treatment. FIG. 3B shows representative fluorescence images of treated mice. FIG. 4C shows tumor growth curve quantification. Data is presented in Total flux (p/s) ±SEM, n=10 per group, **p<0.0001. One-way ANOVA was used to assess the significance at day 49. FIG. 4D shows Kaplan-Meier survival curves of treated mice. n=10 animals per treatment group. *P<0.0001. Log-rank (Mantel-Cox) test was used for curve comparison.

Figures 5, 6A, 6B, 6C:
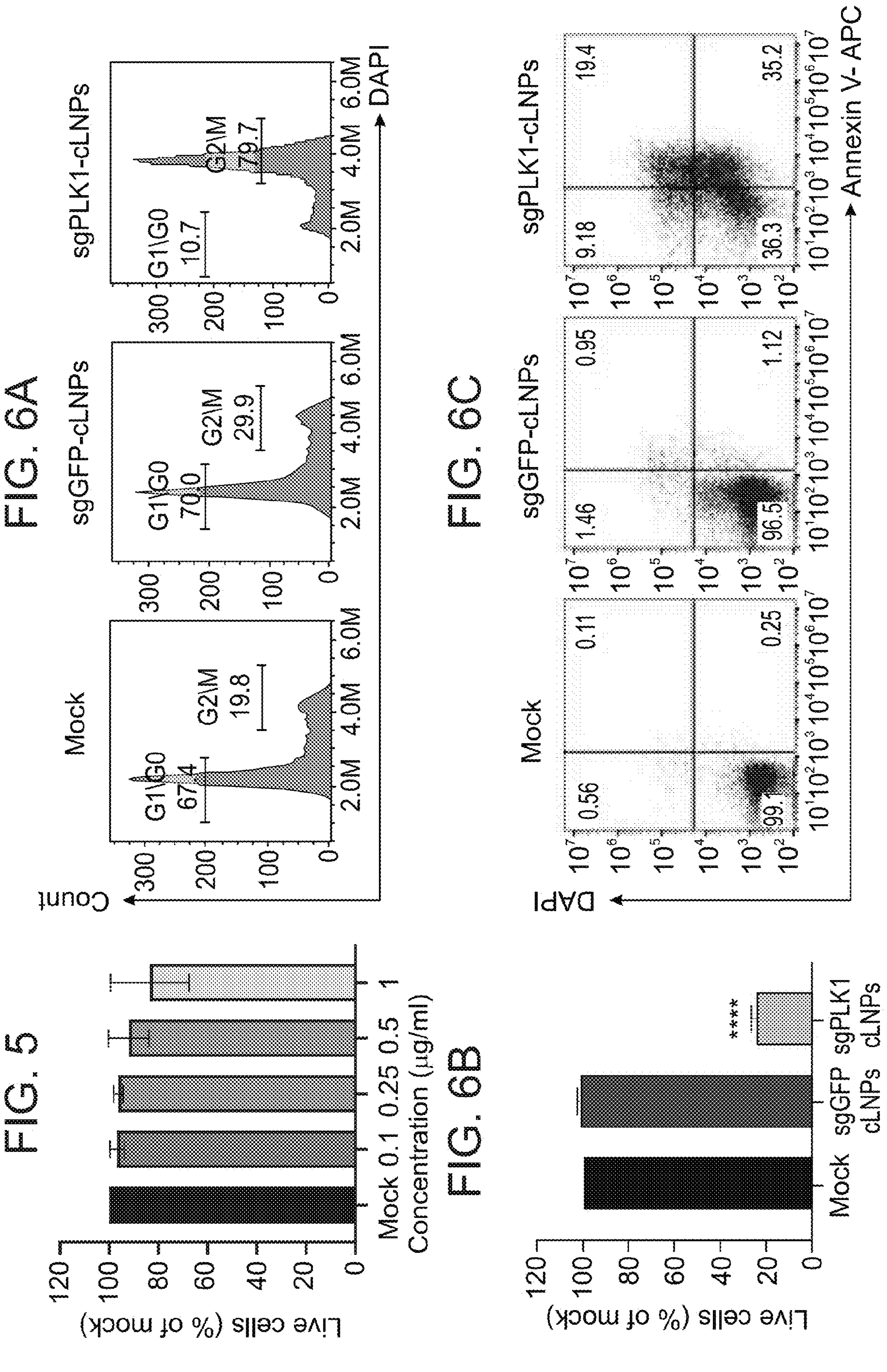

FIG. 5 demonstrates in-vitro safety study of L8-based sgGFP cLNPs in HEK293 cells. HEK293 cells were treated with 0.1-1 μg/ml cLNPs for 72 hours. Cells were stained with DAPI viability dye and analyzed by flow cytometry. Data is representative of 3 independent experiments as biological replicates. p=n.s., one-way ANOVA with Tukey multiple comparison test was used to assess the significance.

FIGS. 6A, 6B and 6C demonstrate in-vitro genome editing leading to cell death of HEK293 cells following transfection with L8-based sgPLK1 cLNPs. FIG. 6A demonstrates cell cycle analysis of HEK293 cells 48 hours post treatment with Mock control, sgGFP-cLNPs or sgPLK1-cLNPs (0.5 μg/ml), as determined by flow cytometry. Data is representative diagram of three independent experiments. FIG. 6B demonstrates viability of HEK293 cells 96 hours post treatment with Mock control, sgGFP-cLNPs or sgPLK1-cLNPs (0.5 μg/ml), as determined by DAPI/AnnexinV assay. Results are presented as the % of Mock treated cells. Data is shown as the mean of ≥three independent experiments, **p<0.0001, one-way ANOVA with Tukey multiple comparison test was used to assess the significance. FIG. 6**C shows representative DAPI/AnnexinV diagrams. Data is representative of three independent experiments.

Figure 7A:
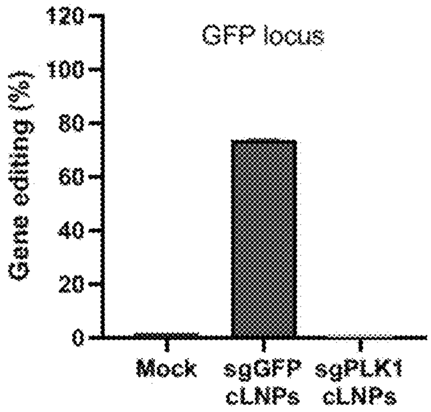
Figure 7B:
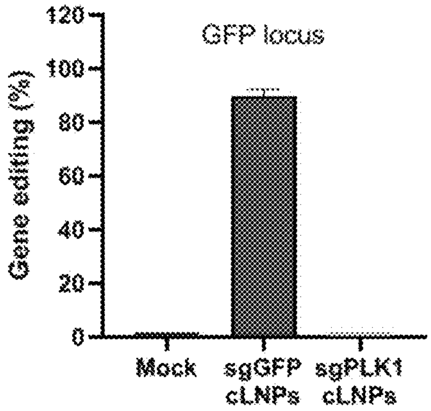

FIGS. 7A-7B demonstrate % of gene editing events in the GFP (FIG. 7A) loci, in 005 (FIG. 7A) and OV8 (FIG. 7B) cells following transfection with L8-based sgGFP cLNPs, as determined by next generation sequencing analysis.

Figures 8A, 8B:
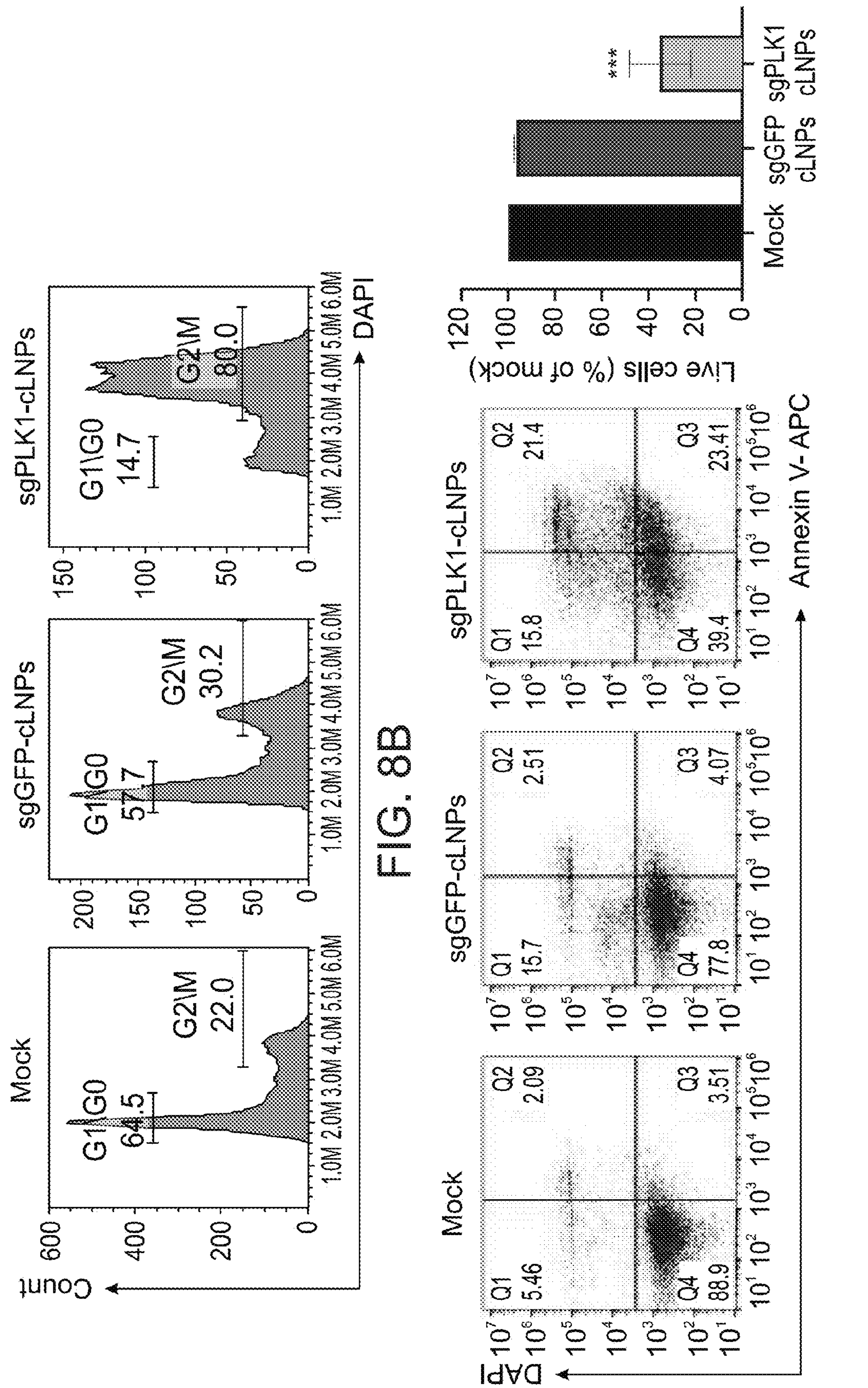
Figures 8C, 8D:
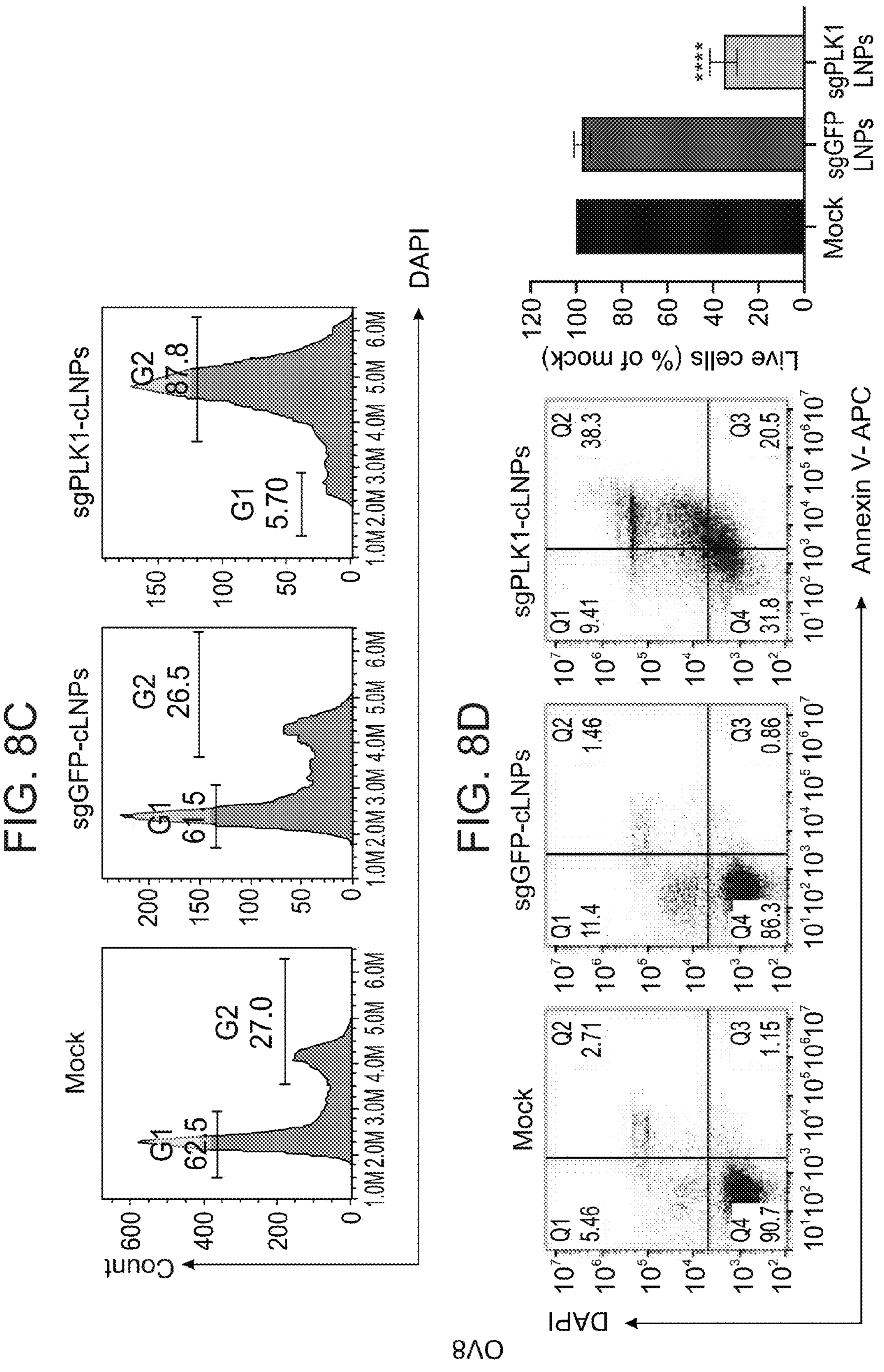

FIGS. 8A, 8B, 8C and 8D demonstrate in-vitro genome editing leading to G2/M cell cycle arrest and cell death in the murine glioblastoma cell line 005 (FIGS. 8A-B) and the human ovarian cancer cell line OV8 (FIGS. 8C-D) following transfection with L8-based sgPLK1 cLNPs. FIGS. 8A and 8C demonstrate cell cycle analysis of 005 cells and OV8, respectively, 48 hours post treatment with Mock control, sgGFP-cLNPs or sgPLK1-cLNPs (005-0.5 μg/ml, OV8-1 μg/ml), as determined by flow cytometry. FIGS. 8B and 8D demonstrate viability of 005 and OV8 cells, respectively, 96 hours post treatment with Mock control, sgGFP-cLNPs or sgPLK1-cLNPs (005-0.5 μg/ml, OV8—1 μg/ml), as determined by DAPI/AnnexinV apoptosis analysis. Shown are representative flow cytometry plots (left) and mean+SD of three independent experiments (right). *p<0.001,**p<0.0001.

Figure 9A:
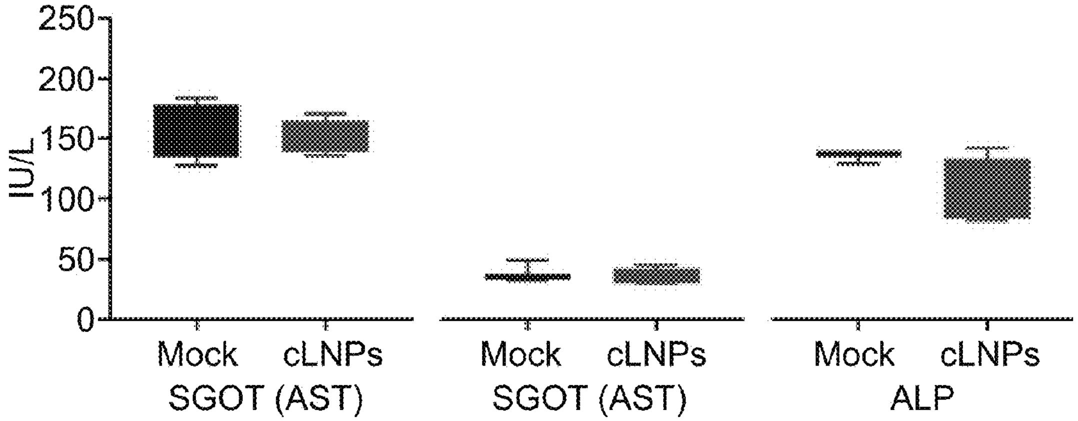
Figure 9B:
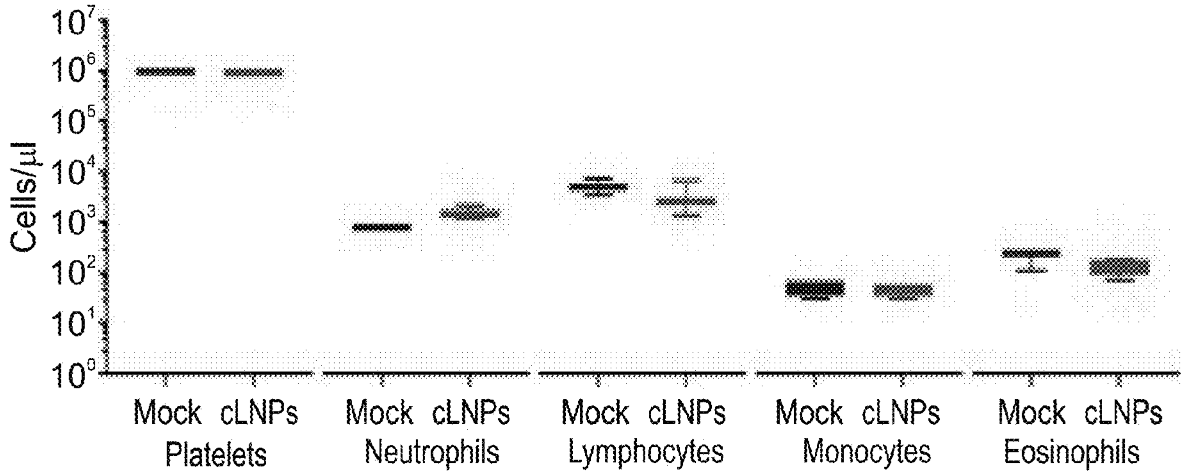
Figure 9C:
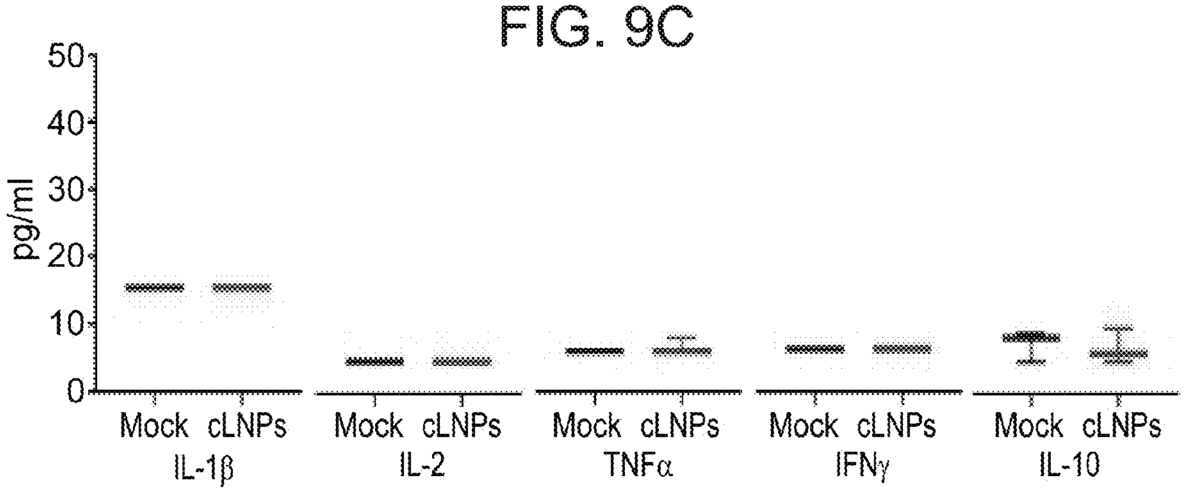

FIGS. 9A, 9B and 9C demonstrate liver toxicity and immunogenicity evaluation following intravenous injection of cLNPs. C57BL/6 Mice were injected intravenously with 1 mg/kg body sgGFP-cLNPs. Liver enzymes elevation in the blood [alanine transaminase (ALT), aspartate aminotransferase (AST), and alkaline phosphatase (ALP)] (FIG.

9A) and total blood counts (FIG. 9B) were evaluated 24 hours post-injection. Immunogenicity was evaluated by elevation in blood levels of the pro and anti-inflammatory cytokines (Interleukin 1β (IL-1β), Interleukin 2 (IL-2), Tumor necrosis factor α (TNF-α), Interferon γ (IFN-γ), and Interleukin 10 (IL-10)) (FIG. 9C). Data is representative of 3 independent experiments as biological replicates. Data is shown as interquartile range (IQR) with a median center line and min to max error bars (FIGS. 9A-B) and mean±s.d. (FIG. 9C), n=3, P=not significant.

Figure 10:
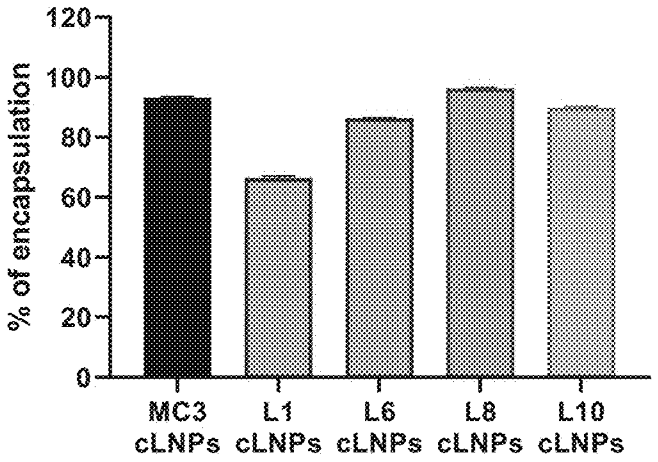

FIG. 10 demonstrates encapsulation efficiency of Cas9 mRNA and GFP sgRNA in MC3-based, L1-based, L6-based, L8-based and L-10-based LNPs, as measured using a RiboGreen assay.

Figure 11:
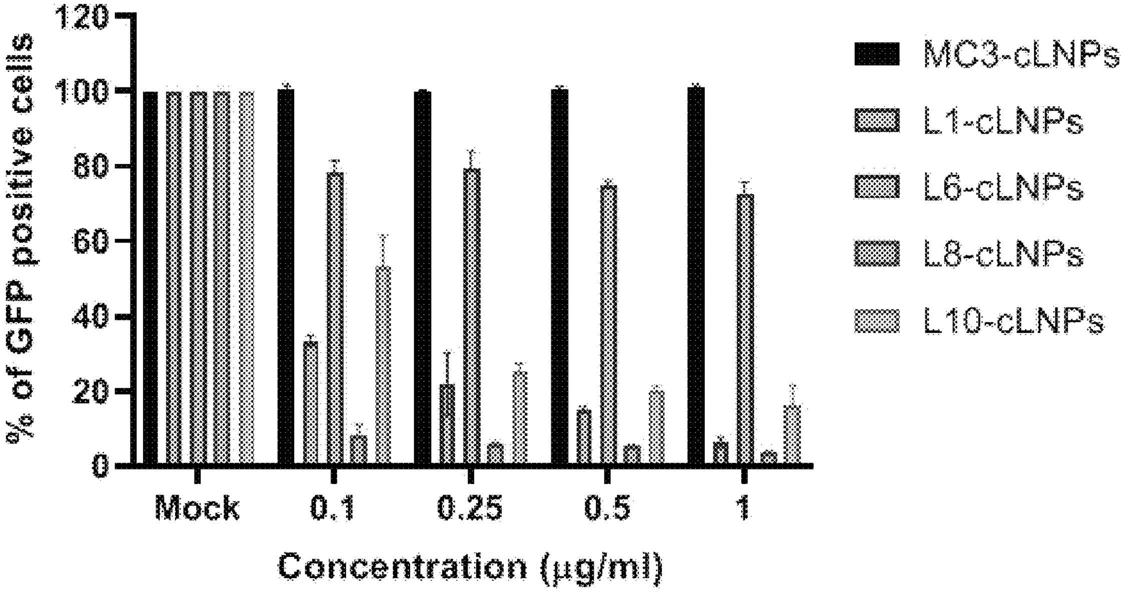

FIG. 11 demonstrates GFP disruption assay in HEK293 cells. HEK293 expressing GFP (HEK/GFP) cells were transfected with increasing concentrations of MC3-based, L1-based, L6-based, L8-based or L-10-based sgGFP cLNPs and the % of GFP positive cells was analyzed 72 hours post transfection by flow cytometry.

Figure 12:
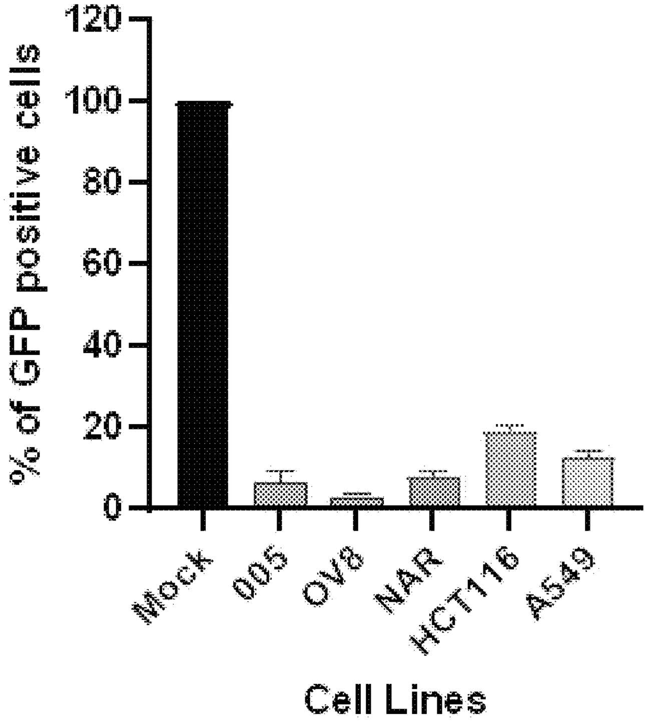

FIG. 12 demonstrates GFP disruption assay in tumor cell lines. 005, OV8, NAR, HCT116 or A549 cell lines were transfected with L8-based sgGFP cLNPs or Mock control and the % of GFP positive cells was analyzed 72 hours post transfection by flow cytometry. Results are presented as the % of Mock treated cells for each cell line.

DESCRIPTION OF SPECIFIC EMBODIMENTS OF THE INVENTION

The present invention, in some embodiments thereof, relates to lipid particles for nucleic acid delivery and clinical applications of same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Polynucleotide- or protein-based therapies are limited by the difficult cellular internalization of these macromolecules. Several delivery systems have been developed and proposed to improve cell permeability of these molecular therapies. Examples of these systems range from cell electroporation to viral delivery, the use of lipid particles (e.g. liposomes, lipid nanoparticles), inorganic compounds (cationic polymers, nanotubes, nanoparticles) and cell-penetrating peptides (CPPs). However, delivering functional large proteins and polynucleotides encoding such proteins to a cell can be problematic. For example, due to the large size of the CRISPR/Cas system Cas9 nuclease (160 kDa, 4300b), its encapsulation, cell delivery and translation using both viral and non-viral delivery systems remains a challenge.

Whilst reducing the present invention to practice, the present inventors have now developed and tested a highly efficient non-viral lipid nanoparticle (LNP) for CRISPR/Cas9 gene editing which showed gene editing of up to 98% in-vitro in multiple cell types and was able to reduce tumor growth and improve survival in two aggressive cancer mice models.

As is illustrated hereinunder and in the examples section, which follows, the present inventors show that LNPs were designed to co-encapsulate Cas9 mRNA and sgRNA, using the gold standard DLin-MC3-DMA (hereinafter MC3) ionizable cationic lipid or an ionizable cationic lipid from a novel ionizable amino lipid library[7], namely lipid8 (L8), lipid10 (L10), lipid1(L1) and lipid6 (L6). (Example 1 and 5, FIGS. 1A-C). The generated lipid nanoparticles encapsulating the Cas9 mRNA and sgRNA are referred to herein as CRISPR LNPs or cLNPs. The generated L8-based, L10-based and L1-based cLNPs induced in-vitro gene disruption in transfected cells whereas MC3-based or L6-based LNPs did not (Examples 2 and 5, FIGS. 1D-I, 5 and 10-12). Moreover, using gRNA targeting the PLK1 kinase, the L8-based cLNPs induced in-vitro cell death in multiple cell lines, including glioblastoma and ovarian cancer lines (Example 3, FIGS. 1H-I, 2A-F, and 6A-8D). Furthermore, L8-based cLNPs were able to induce in-vivo gene disruption leading to reduced tumor growth and improved survival in glioblastoma and ovarian cancer mice models, suggesting they can be used for therapeutic genome editing (Example 4, FIGS. 3A-4D and 9A-C).

Consequently, specific embodiments of the present teachings suggest delivery of polynucleotides encoding large proteins using lipid particles comprising specific cationic lipids.

Thus, according to a first aspect of the present invention, there is provided a lipid particle comprising a cationic lipid represented by Formula I as defined herein encapsulating a nucleic acid sequence, wherein said nucleic acid sequence encodes a protein having a length of at least 500 amino acids.

According to an additional or an alternative aspect of the present invention, there is provided a method of preparing a lipid particle for delivery of a nucleic acid sequence, the method comprising encapsulating a nucleic acid sequence in a lipid particle comprising a cationic lipid represented by Formula I as defined herein, wherein said nucleic acid sequence encodes a protein having a length of at least 500 amino acids.

As used herein, “lipid particle” refers to a nano to micro structure comprising lipids, which is not a biological cell.

The particle may be a synthetic carrier, gel or other object or material having an external surface which is capable of being loadable with (e.g., encapsulated in) a nucleic acid sequence. The particle may be either polymeric or non-polymeric preparation.

Exemplary particles that may be used according to specific embodiments of the invention include, but are not limited to, polymeric particles, microcapsules, liposomes, microspheres, microemulsions, nanoparticles, nanocapsules, nano-spheres, nano-liposomes, nano-emulsions and nanotubes.

Suitable particles in accordance with some embodiments of the invention are preferably non-toxic.

According to specific embodiments, the particle is a liposome. As used herein and as recognized in the art, liposomes include any synthetic (i.e., not naturally occurring) structure composed of lipid bilayers, which enclose a volume. Liposomes include emulsions, foams, micelles, insoluble monolayers, liquid crystals, phospholipid dispersions, lamellar layers and the like. The liposomes may be prepared by any of the known methods in the art [Monkkonen, J. et al., 1994, J. Drug Target, 2:299-308; Monkkonen, J. et al., 1993, Calcif. Tissue Int., 53:139-145; Lasic D D., Liposomes Technology Inc., Elsevier, 1993, 63-105. (chapter 3); Winterhalter M, Lasic D D, Chem Phys Lipids, 1993 September; 64(1-3):35-43].

The diameter of the liposomes used preferably ranges from 20-200 nm and more preferably from 20-100 nm. For sizing liposomes, extrusion, homogenization or exposure to ultrasound irradiation may be used, Homogenizers which may be conveniently used include microfluidizers (produced by Microfluidics of Boston, MA, USA) or microfluidic micro mixer (Precision NanoSystems, Vancouver, BC, Canada). In a typical homogenization procedure, liposomes are recirculated through a standard emulsion homogenizer until selected liposomes sizes are observed. The particle size distribution can be monitored by conventional laser beam particle size discrimination. Extrusion of liposomes through a small-pore polycarbonate membrane or an asymmetric ceramic membrane is an effective method for reducing liposome sizes to a relatively well defined size distribution. Typically, the suspension is cycled through the membrane one or more times until the desired liposome size distribution is achieved. The liposomes may be extruded through successively smaller pore membranes to achieve a gradual reduction in liposome size. The liposomes may be unilamellar or may be multilamellar. Unilamellar liposomes may be preferred in some instances as they represent a larger surface area per lipid mass.

According to a particular embodiment, the particle is a nanoparticle.

As used herein, the term "nanoparticle" refers to a particle or particles having an intermediate size between individual atoms and macroscopic bulk solids. Generally, nanoparticle has a characteristic size (e.g., diameter for generally spherical nanoparticles, or length for generally elongated nanoparticles) in the sub-micrometer range, e.g., from about 1 nm to about 500 nm, or from about 1 nm to about 200 nm, or of the order of 10 nm, e.g., from about 1 nm to about 100 nm. According to specific embodiments, the particle is a nanoparticle having a size of 30-150 nm.

The nanoparticles may be of any shape, including, without limitation, elongated particle shapes, such as nanowires, or irregular shapes, in addition to more regular shapes, such as generally spherical, hexagonal and cubic nanoparticles. According to one embodiment, the nanoparticles are generally spherical.

Non-limiting examples of lipid nanoparticles that can be used with specific embodiments of the present invention and methods of producing same are further described hereinbelow and in the Examples section which follows, and also in e.g. Ramishetti et al. Adv Mater. 2020 Jan. 30:e1906128, International Patent Application publication Nos. WO2016/189532, WO2018/015881 and WO2018087753, WO2017194454 and US Patent Application Publication no. US20130245107, the contents of which are fully incorporated herein by reference.

The nanoparticle may be prepared by any of the methods known in the art, such as disclosed in e.g. Jayaraman et al. Angew chem. July 2012, Semple et al. Nat Biotech. 2010, Kauffman et al. Nano Lett, October 2015; and in the Examples section which follows.

The core of the particle may be hydrophilic or hydrophobic. The core of the lipid nanoparticle may comprise some lipids, such that it is not fully hydrophilic.

According to specific embodiments, the core of the particle is hydrophobic.

According to specific embodiments, the core of the particle is hydrophilic.

It will be appreciated that combinations of different lipids may be used to fabricate the particles disclosed herein, including a mixture of more than one cationic lipid, a mixture of at least one cationic lipid and at least one anionic lipid, a mixture of at least one cationic lipid and at least one neutral lipid and additional combinations of the above.

According to some exemplary embodiments, the plurality of lipids of the lipid particles may be of natural or synthetic source and may be selected from, but not limited to: cationic lipids, phosphatidylethanolamines, ionized lipids, membrane stabilizing lipids, phospholipids, and the like, or combinations thereof. Each possibility represents a separate embodiment of the present invention.

In some embodiments, the membrane stabilizing lipids may be selected from, but not limited to: cholesterol, phospholipids (such as, for example, phosphatidylcholine, phosphatidylethanolamine, phosphatidylinositol, phosphatidylserine, phosphatidylglycerol, diphosphatidylglycerols), cephalins, sphingolipids (sphingomyelins and glycosphingolipids), glycoglycerolipids, and combinations thereof. Each possibility represents a separate embodiment of the present invention.

In some embodiments, the phosphatidylethanolamines may be selected from, but not limited to: 1,2-dilauroyl-L-phosphatidyl-ethanolamine (DLPE), 2-Dioleoyl-sn-glycero-3-phosphoethanolamine (DOPE), 1,2-Diphytanoyl-sn-glycero-3-phosphoethanolamine (DPhPE) 1,3-Dipalmitoyl-sn-glycero-2-phosphoethanolamine (1,3-DPPE), 1-Palmitoyl-3-oleoyl-sn-glycero-2-phosphoethanolamine (1,3-POPE), Biotin-Phosphatidylethanolamine, 1,2-Dimyristoyl-sn-glycero-3-phosphoethanolamine (DMPE), Dipalmitoylphosphatidylethanolamine (DPPE), 1,2-Distearoyl-sn-glycero-3-phosphoethanolamine (DSPE) combinations thereof. In some embodiments, the Phosphatidylethanolamines may be conjugated to a PEG-Amine derivative. Each possibility represents a separate embodiment of the present invention.

In addition, according to specific embodiments, polymer-lipid based formulations may be used.

There are numerous polymers which may be attached to lipids. Polymers typically used as lipid modifiers include, without being limited thereto: polyethylene glycol (PEG), polysialic acid, polylactic (also termed polylactide), polyglycolic acid (also termed polyglycolide), apolylactie-polyglycolic acid' polyvinyl alcohol, polyvinylpyrrolidone, polymethoxazoline, polyethyloxazoline, polyllydroxyetlyloxazolille, solyhydroxypryloxazoline, polyaspartarllide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose.

The polymers may be employed as homopolymers or as block or random copolymers.

The particles may also include other components. Examples of such other components includes, without being limited thereto, fatty alcohols, fatty acids, and/or cholesterol esters or any other pharmaceutically acceptable excipients which may affect the surface charge, the membrane fluidity and assist in the incorporation of the biologically active lipid into the lipid assembly. Examples of sterols include cholesterol, cholesterol hemisuccinate, cholesterol sulfate, or any other derivatives of cholesterol. Lipid assemblies according to specific embodiments the invention include either those which form a micelle (typically when the assembly is absent from a lipid matrix) or those which form a liposome (typically, when a lipid matrix is present).

According to one embodiment, the lipid phase comprises phospholipids.

The phospholipids may be a glycerophospholipid. Examples of glycerophospholipid include, without being limited thereto, phosphatidylglycerol (PG) including dimyristoyl phosphatidylglycerol (DMPG); phosphatidylcholine (PC), including egg yolk phosphatidylcholine and dimyristoyl phosphatidylcholine (DMPC), phosphatidic acid (PA), phosphatidylinositol (PI), phosphatidylserine (PS) and sphingomyelin (SM) and derivatives of the same.

The lipid particles disclosed herein comprise cationic lipids (monocationic or polycationic lipids). Cationic lipids typically comprise a lipophilic moiety, such as a sterol or a glycerol backbone to which two acyl or two alkyl, or one acyl and one alkyl chain contribute the hydrophobic region of the amphipathic molecule, to form a lipid having an overall net positive charge. According to specific embodiments, the particles comprise cationic lipids other than those represented by Formula I as defined herein. Non-limiting examples of cationic lipids that may be used with specific embodiments of the invention include, 1,2-dimyristoyl-3-trimethylammonium propane (DMTAP) 1,2-dioleyloxy-3-(trimethylanino) propane (DOTAP), N-[-1-(2,3,-ditetradecyloxy)propyl]-N,N-dimethyl-N-hydroxyethylammonium bromide (DMRIE), N-[1-(2,3,-dioleyloxy)propyl]-N,N-dimethyl-N-hydroxy ethyl-ammonium bromide (DORIE), N-[1-(2,3-dioleyloxy) propyl]; —N,N,N-trimethylammonium chloride (DOTMA); 3; N-(N',N'-dimethylaminoethane) carbamoly]; cholesterol (DC-Chol), and I dimethyl-dioctadecylammonium (DDAB), N-[2-[[2,5-bis[3-aminopropyl)amino]-1-oxopentyl]amino] ethyl]N,N dimethul-2,3 bis (1-oXo-9-octadecenyl) oXy];-1 propanaminium (DOSPA), ceramide carbamoyl spermine (CCS), D-Lin-MC3-DMA (Cas No. 1224606-06-7).

According to other specific embodiments, the particles are devoid of cationic lipids other than those represented by Formula I as defined herein.

The cationic lipids may be used alone, in combination with cholesterol, with neutral phospholipids or other known lipid assembly components. In addition, the cationic lipids may form part of a derivatized phospholipids such as the neutral lipid dioleoylphosphatidyl ethanolamine (DOPE) derivatized with polylysine to form a cationic lipopolymer.

According to specific embodiments, the polymer used for fabricating the particles is biocompatible and biodegradable, such as poly(DL-lactide-co-glycolide) polymer (PLGA). However, additional polymers which may be used for fabricating the particles include, but are not limited to, PLA (polylactic acid), and their copolymers, polyanhydrides, polyalkyl-cyanoacrylates (such as polyisobutylcyanoacrylate), polyethyleneglycols, polyethyleneoxides and their derivatives, chitosan, albumin, gelatin and the like.

The particles of the present invention may be modified to enhance their circulatory half-life (e.g. by PEGylation) to reduce their clearance, to prolong their scavenging time-frame and to allow antibody binding. The PEG, which is incorporated into the particles, may be characterized by any of various combinations of chemical composition and/or molecular weight, depending on the application and purpose.

According to some embodiments, the particle includes one or more PEG derivatives. According to specific embodiments, the PEG or PEG derivative may be conjugated to as, a lipid. Non-limiting examples of PEG derivative include PEG-DMG 3-N-(-methoxy poly(ethylene glycol) 2000)carbamoyl-1,2-dimyrisyl glycerol, PEG-cDMA 3-N-(-methoxy poly(ethylene glycol)2000)carbamoyl-1,2-dimyristyloxy-propylamine; PEG-cDSA, 3-N-(-methoxy polyethylene glycol)2000)carbamoyl-1,2-distearyloxy-propylamine, DSPE-PEG, PEG-maleimide, DSPE-PEG-maleimide, or combinations thereof.

According to some embodiments, the lipid phase may comprise about 30-60% (mol) cationic lipids. For example, the cationic lipid(s) may comprise about 40-50% (mol) of the lipid phase.

According to some embodiments, the lipid phase may comprise about 20-70% (mol) membrane stabilizing lipids. For example, the membrane stabilizing lipids may comprise about 40-60% of the lipid phase. In some embodiments, more than one type of membrane stabilizing lipid may be used in the lipid phase. For example, the membrane stabilizing lipid may include cholesterol (being about 30-50% (mol) of the lipid phase), and a phospholipid (such as, for example, DSPC), that may be about 5-15% (mol) of the lipid phase.

According to some embodiments, the lipid phase may comprise about 0.01-3% (mol) of PEG-maleimide (optionally conjugated to a lipid). For example, the PEG-maleimide may comprise about 0.05-0.6% of the lipid mixture.

According to some embodiments, an additional PEG-derivative (conjugated to a lipid) may comprise about 0.5-10% of the lipid phase composition.

According to exemplary embodiments, the particles may be comprised of a cationic lipid (e.g., a cationic lipid represented by Formula I as defined herein), cholesterol, 1,2-Distearoyl-sn-glycero-3-phosphocholine (DSPC), PEG derivative (such as DMG-PEG) and PEG-maleimide conjugated to a lipid (such as DSPE-PEG-maleimide); at various mol/mol ratios. For example, the lipid phase may be comprised of: cationic lipid (e.g., a cationic lipid represented by Formula I as defined herein)/DSPC/Chol/DMG-PEG/DSPE-PEG-maleimide (mol/mol 50:10.5:38:1.4:0.1).

According to the present embodiments, the particle comprises one or more cationic lipids, which are collectively represented by Formula I:

Formula I

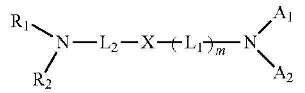

wherein:

m is 0 or 1

A1 and A2 are each independently a saturated or unsaturated linear, non-branched, alkylene chain, of at least 8 carbon atoms in length;

L1 is a first linking group which an alkylene of 1 to 4 carbon atoms in length;

X is —O—C(═O)— or —NH—C(═O);

L2 is a second linking group which is an alkylene of 1 to 4 carbon atoms in length; and R1 and R2 are each independently hydrogen, alkyl or cycloalkyl, or, alternatively, R1 and R2 form together with the nitrogen to which they are attached a heteroalicyclic ring, provided that when X is —O—C(═O)—, m is 1.

In some of any of the embodiments of Formula I, X is —O—C(═O)— and the cationic lipid is represented by Formula Ia:

Formula Ia

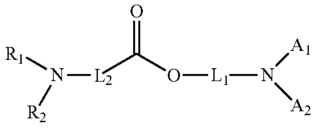

wherein A1, A2, L1, L2, R1 and R2 are as defined for Formula I.

In some of the embodiments of Formula Ia, L1 is an unsubstituted alkylene.

In some of the embodiments of Formula Ia, L1 is an alkylene being 2 carbon atoms in length.

In some of the embodiments of Formula Ia, L1 is an unsubstituted alkylene being 2 carbon atoms in length.

In some of any of the embodiments of Formula I, X is —NH—C(=O)— and m is 0, and the cationic lipid is represented by Formula Ib:

Formula Ib

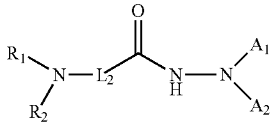

wherein A1, A2, L2, R1 and R2 are as defined for Formula I.

In some of any of the embodiments of Formula I, Ia or Ib, L2 is an alkylene chain of 3 carbon atoms in length.

In some of any of the embodiments of Formula I, Ia or Ib, L2 is an unsubstituted alkylene chain.

In some of any of the embodiments of Formula I, Ia or Ib, L2 is an alkylene chain of 3 carbon atoms in length, and is unsubstituted.

In some of any of the embodiments of Formula I, Ia or Ib, at least one, and preferably both, of R1 and R2 is alkyl, preferably a short alkyl, of 1 to 4 carbon atoms in length, more preferably methyl.

In some of any of the embodiments of Formula I, Ia or Ib, at least one, and preferably both, of R1 and R2 is methyl.

In some of any of the embodiments of Formula I, Ia or Ib, each of R1 and R2 is alkyl, and in some embodiments, each of R1 and R2 is methyl.

In some of any of the embodiments of Formula I and Ia, R1 and R2 form together a heteroalicyclic ring.

The heteroalicyclic ring is preferably a five-, six- or seven-membered ring, preferably a six-membered ring. The heteroalicyclic ring can include an additional heteroatom, other than the nitrogen to which R1 and R2 are attached. In exemplary embodiments, the additional heteroatom is another nitrogen atom. In exemplary embodiments, R1, R2 and N form together a piperazine.—N(R1)(R2) can alternatively form together any other heteroalicyclic group, such as those exemplified hereinunder, under the definition of a "heteroalicyclic".

In some of any of the embodiments of Formula Ib, each of R1 and R2 is alkyl, and in some embodiments, each of R1 and R2 is methyl.

In some of any of the embodiments of Formula I, Ia or Ib, A1 and A2 can be the same or different and are preferably the same.

In some of any of the embodiments of Formula I, Ia or Ib, at least one, and preferably both, of A1 and A2 is an unsaturated alkylene chain.

In some of any of the embodiments of Formula I, Ia or Ib, at least one, and preferably both, of A1 and A2 is an alkylene chain of from 8 to 40, or from 8 to 30, or from 10 to 30 or from 12 to 30, or from 14 to 30, carbon atoms in length, In some of any of the embodiments of Formula I, Ia or Ib, at least one, and preferably both, of A1 and A2 is an unsubstituted alkylene chain.

In some of any of the embodiments of Formula I, Ia or Ib, at least one, and preferably both, of A1 and A2 is an unsubstituted unsaturated alkylene chain.

In some of any of the embodiments of Formula I, Ia or Ib, at least one, and preferably both, of A1 and A2 is an unsubstituted, unsaturated alkylene chain, of from 8 to 40, or from 8 to 30, or from 10 to 30 or from 12 to 30, or from 14 to 30, carbon atoms in length.

Each of A1 and A2 can independently be a hydrocarbon residue of a fatty acid, which can also be referred to as a hydrocarbon derived from a fatty acid, that is, the hydrocarbon moiety that is attached to the carboxylic acid in a fatty acid, optionally having another methylene group (instead of the carboxylic acid group).

The fatty acid can be a saturated or unsaturated fatty acid, and is preferably an unsaturated fatty acid.

Exemplary fatty acids in the context of these embodiments include, but are not limited to, saturated or unsaturated fatty acids that have more than 10 carbon atoms, preferably between 12 and 24 carbon atoms, such as, but not limited to, myristic acid, lauric acid, palmitic acid, stearic acid, oleic acid, linoleic acid, linolenic acid, arachidonic acid, etc.

Whenever an alkylene chain is unsaturated, it may include 1, 2, 3 or more unsaturated bonds therewithin. The unsaturated bonds can each independently have a cis or trans configuration.

In exemplary embodiments of Formula I, Ia or Ib, at least one, and preferably both, of A1 and A2 is an unsaturated alkylene having two or more unsaturated bonds, and in some of these exemplary embodiments, each of the unsaturated bonds has a cis-configuration.

In exemplary embodiments of Formula I, Ia or Ib, at least one, and preferably both, of A1 and A2 is a residue of linoleic acid, that is, is (9Z,12Z)-octadeca-9,12-dienyl.

An exemplary cationic lipid of Formula Ib is presented herein as Lipid 1.

An exemplary cationic lipid of Formula Ia, in which R1 and R2 are each methyl, is presented herein as Lipid 8.

An exemplary cationic lipid of Formula Ia, in which R1 and R2 form together a heteroalicyclic ring is presented herein as Lipid 10.

According to some of any of the embodiments described herein, any of the cationic lipids according to the present embodiments can be in a form of a salt thereof, preferably a pharmaceutically acceptable salt thereof.

As used herein, the phrase "pharmaceutically acceptable salt" refers to a charged species of the parent compound (herein a catrionic lipid as described herein, e.g., a cationic lipid of Formula I) and its counter-ion, which is typically used to modify the solubility characteristics of the parent compound and/or to reduce any significant irritation to an organism by the parent compound, and/or to improve its stability, while not abrogating the biological activity and properties of the compound. A pharmaceutically acceptable salt of a compound as described herein can alternatively be formed during the synthesis of the compound, e.g., in the course of isolating the compound from a reaction mixture or re-crystallizing the compound.

In the context of some of the present embodiments, a pharmaceutically acceptable salt of the compounds described herein may optionally be an acid addition salt comprising at least one basic (e.g., an amine or an amine-containing group) group of the compound which is in a positively charged form (e.g., wherein the basic group is protonated), in combination with at least one counter-ion, derived from the selected base, that forms a pharmaceutically acceptable salt.

The acid addition salts of the compounds described herein may therefore be complexes formed between one or more basic groups of the compound and one or more equivalents of an acid.

Depending on the stoichiometric proportions between the charged group(s) in the compound and the counter-ion in the salt, the acid additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

An example, without limitation, of a pharmaceutically acceptable salt would be an ammonium cation and an acid addition salt thereof.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined herein.

The present embodiments further encompass any enantiomers, diastereomers, prodrugs, solvates, hydrates and/or pharmaceutically acceptable salts of the compounds described herein (e.g., cationic lipids of Formula I as described herein).

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment, which by itself has handedness, such as all living systems. In the context of the present embodiments, a compound may exhibit one or more chiral centers, each of which exhibiting an R- or an S-configuration and any combination, and compounds according to some embodiments of the present invention, can have any their chiral centers exhibit an R- or an S-configuration.

The term "diastereomers", as used herein, refers to stereoisomers that are not enantiomers to one another. Diastereomerism occurs when two or more stereoisomers of a compound have different configurations at one or more, but not all of the equivalent (related) stereocenters and are not mirror images of each other. When two diastereoisomers differ from each other at only one stereocenter they are epimers. Each stereo-center (chiral center) gives rise to two different configurations and thus to two different stereoisomers. In the context of the present invention, embodiments of the present invention encompass compounds with multiple chiral centers that occur in any combination of stereo-configuration, namely any diastereomer.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolyzed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the compound of the present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

Herein throughout, the phrase "linking moiety" or "linking group" describes a group that connects two or more moieties or groups in a compound. A linking moiety is typically derived from a bi- or tri-functional compound, and can be regarded as a bi- or tri-radical moiety, which is connected to two or three other moieties, via two or three atoms thereof, respectively.

Exemplary linking moieties include a hydrocarbon moiety or chain, optionally interrupted by one or more heteroatoms, as defined herein, and/or any of the chemical groups listed below, when defined as linking groups.

When a chemical group is referred to herein as "end group", it is to be interpreted as a substituent, which is connected to another group via one atom thereof.

Herein throughout, the term "hydrocarbon" collectively describes a chemical group composed mainly of carbon and hydrogen atoms. A hydrocarbon can be comprised of alkyl, alkene, alkyne, aryl, and/or cycloalkyl, each can be substituted or unsubstituted, and can be interrupted by one or more heteroatoms. The number of carbon atoms can range from 2 to 20, and is preferably lower, e.g., from 1 to 10, or from 1 to 6, or from 1 to 4. A hydrocarbon can be a linking group or an end group.

As used herein, the term "amine" describes both a —NR'R" group and a —NR'— group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

Further alternatively, R' and R" form together a heteroalicyclic nitrogen-containing ring.

The amine group as described herein can be in a protonated or an ammonium form, as described herein.

The term "alkyl" describes a saturated aliphatic hydrocarbon including straight chain and branched chain groups. Preferably, the alkyl group has 1 to 30, or 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. The alkyl group may be substituted or unsubstituted.

The alkyl group can be an end group, as this phrase is defined hereinabove, wherein it is attached to a single adjacent atom, or a linking group, as this phrase is defined hereinabove, which connects two or more moieties via at least two carbons in its chain. When the alkyl is a linking group, it is also referred to herein as "alkylene" or "alkylene chain".

Alkene and Alkyne, as used herein, are an alkyl, as defined herein, which contains one or more double bond or triple bond, respectively.

The term "cycloalkyl" describes an all-carbon monocyclic ring or fused rings (i.e., rings which share an adjacent pair of carbon atoms) group where one or more of the rings does not have a completely conjugated pi-electron system. Examples include, without limitation, cyclohexane, adamantine, norbornyl, isobornyl, and the like. The cycloalkyl group may be substituted or unsubstituted.

The cycloalkyl group can be an end group, as this phrase is defined hereinabove, wherein it is attached to a single adjacent atom, or a linking group, as this phrase is defined hereinabove, connecting two or more moieties at two or more positions thereof.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofurane, tetrahydropyrane, morpholino, oxalidine, and the like.

The heteroalicyclic may be substituted or unsubstituted. The heteroalicyclic group can be an end group, as this phrase is defined hereinabove, where it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

Any one of the amine groups described herein is presented as a free base form thereof, but is meant to encompass an ionized form thereof at physiological pH, and/or within a salt thereof, e.g., a pharmaceutically acceptable salt thereof, as described herein.

Whenever an alkyl, cycloalkyl, aryl, alkaryl, heteroaryl, heteroalicyclic, acyl and any other moiety as described herein is substituted, it includes one or more substituents, each can independently be, but are not limited to, hydroxy, alkoxy, thiohydroxy, thioalkoxy, aryloxy, thioaryloxy, alkaryl, alkenyl, alkynyl, sulfonate, sulfoxide, thiosulfate, sulfate, sulfite, thiosulfite, phosphonate, cyano, nitro, azo, sulfonamide, carbonyl, thiocarbonyl, C-carboxylate, O-carboxylate, N-thiocarbamate, O-thiocarbamate, oxo, thiooxo, oxime, acyl, acyl halide, azo, azide, urea, thiourea, N-carbamate, O-carbamate, C-amide, N-amide, guanyl, guanidyl, hydrazine and hydrazide, as these terms are defined herein.

The term "halide" and "halo" describes fluorine, chlorine, bromine or iodine.

The term "haloalkyl" describes an alkyl group as defined above, further substituted by one or more halide.

The term "sulfate" describes a $—O—S(=O)_2—OR'$ end group, as this term is defined hereinabove, or an $—O—S(=O)_2—O—$ linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)—OR' end group or an —S(=O)—O— group linking group, as these phrases are defined hereinabove, where R' is as defined hereinabove.

The term "sulfoxide" or "sulfinyl" describes a —S(=O)R' end group or an —S(=O)— linking group, as these phrases are defined hereinabove, where R' is as defined hereinabove.

The term "sulfonate" describes a $—S(=O)_2—R'$ end group or an $—S(=O)_2—$ linking group, as these phrases are defined hereinabove, where R' is as defined herein.

The term "S-sulfonamide" describes a $—S(=O)_2—NR'R''$ end group or a $—S(=O)_2—NR'—$ linking group, as these phrases are defined hereinabove, with R' and R" as defined herein.

The term "N-sulfonamide" describes an $R'S(=O)_2—NR''—$ end group or a $—S(=O)_2—NR'—$ linking group, as these phrases are defined hereinabove, where R' and R" are as defined herein.

The term "disulfide" refers to a —S—SR' end group or a —S—S— linking group, as these phrases are defined hereinabove, where R' is as defined herein.

The term "phosphonate" describes a —P(═O)(OR')(OR") end group or a —P(═O)(OR') (O)-linking group, as these phrases are defined hereinabove, with R' and R" as defined herein.

The term "thiophosphonate" describes a —P(═S)(OR')(OR") end group or a —P(═S)(OR')(O)— linking group, as these phrases are defined hereinabove, with R' and R" as defined herein.

The term "phosphinyl" describes a —PR'R" end group or a —PR'-linking group, as these phrases are defined hereinabove, with R' and R" as defined hereinabove.

The term "phosphine oxide" describes a —P(═O)(R')(R") end group or a —P(═O)(R')— linking group, as these phrases are defined hereinabove, with R' and R" as defined herein.

The term "phosphine sulfide" describes a —P(═S)(R')(R") end group or a —P(═S)(R')— linking group, as these phrases are defined hereinabove, with R' and R" as defined herein.

The term "phosphite" describes an —O—PR'(═O)(OR") end group or an —O—PH(═O)(O)-linking group, as these phrases are defined hereinabove, with R' and R" as defined herein.

The term "carbonyl" or "carbonate" as used herein, describes a —C(═O)—R' end group or a —C(═O)— linking group, as these phrases are defined hereinabove, with R' as defined herein.

The term "thiocarbonyl" as used herein, describes a —C(═S)—R' end group or a —C(═S)-linking group, as these phrases are defined hereinabove, with R' as defined herein.

The term "oxo" as used herein, describes a (═O) group, wherein an oxygen atom is linked by a double bond to the atom (e.g., carbon atom) at the indicated position.

The term "thiooxo" as used herein, describes a (═S) group, wherein a sulfur atom is linked by a double bond to the atom (e.g., carbon atom) at the indicated position.

The term "oxime" describes a ═N—OH end group or a ═N—O— linking group, as these phrases are defined hereinabove.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The "hydroxyalkyl" is also referred to herein as "alcohol", and describes an alkyl, as defined herein, substituted by a hydroxy group.

The term "cyano" describes a —C≡N group.

The term "isocyanate" describes an —N═C═O group.

The term "isothiocyanate" describes an —N═C═S group.

The term "nitro" describes an $—NO_2$ group.

The term "acyl halide" describes a —(C═O)R"" group wherein R"" is halide, as defined hereinabove.

The term "azo" or "diazo" describes an —N═NR' end group or an —N═N— linking group, as these phrases are defined hereinabove, with R' as defined hereinabove.

The term "peroxo" describes an —O—OR' end group or an —O—O— linking group, as these phrases are defined hereinabove, with R' as defined hereinabove.

The term "carboxylate" as used herein encompasses C-carboxylate and O-carboxylate.

The term "C-carboxylate" describes a —C(═O)—OR' end group or a —C(═O)—O— linking group, as these phrases are defined hereinabove, where R' is as defined herein.

The term "O-carboxylate" describes a —OC(═O)R' end group or a —OC(═O)— linking group, as these phrases are defined hereinabove, where R' is as defined herein.

A carboxylate can be linear or cyclic. When cyclic, R' and the carbon atom are linked together to form a ring, in C-carboxylate, and this group is also referred to as lactone. Alternatively, R' and O are linked together to form a ring in O-carboxylate. Cyclic carboxylates can function as a linking group, for example, when an atom in the formed ring is linked to another group.

The term "thiocarboxylate" as used herein encompasses C-thiocarboxylate and O-thiocarboxylate.

The term "C-thiocarboxylate" describes a —C(═S)—OR' end group or a —C(═S)—O— linking group, as these phrases are defined hereinabove, where R' is as defined herein.

The term "O-thiocarboxylate" describes a —OC(═S)R' end group or a —OC(═S)— linking group, as these phrases are defined hereinabove, where R' is as defined herein.

A thiocarboxylate can be linear or cyclic. When cyclic, R' and the carbon atom are linked together to form a ring, in C-thiocarboxylate, and this group is also referred to as thiolactone. Alternatively, R' and O are linked together to form a ring in O-thiocarboxylate. Cyclic thiocarboxylates can function as a linking group, for example, when an atom in the formed ring is linked to another group.

The term "carbamate" as used herein encompasses N-carbamate and O-carbamate.

The term "N-carbamate" describes an R"OC(═O)—NR'—end group or a —OC(═O)—NR'—linking group, as these phrases are defined hereinabove, with R' and R" as defined herein.

The term "O-carbamate" describes an —OC(═O)—NR'R" end group or an —OC(═O)—NR'— linking group, as these phrases are defined hereinabove, with R' and R" as defined herein.

A carbamate can be linear or cyclic. When cyclic, R' and the carbon atom are linked together to form a ring, in O-carbamate. Alternatively, R' and O are linked together to form a ring in N-carbamate. Cyclic carbamates can function as a linking group, for example, when an atom in the formed ring is linked to another group.

The term "carbamate" as used herein encompasses N-carbamate and O-carbamate.

The term "thiocarbamate" as used herein encompasses N-thiocarbamate and O-thiocarbamate.

The term "O-thiocarbamate" describes a —OC(═S)—NR'R" end group or a —OC(═S)—NR'— linking group, as these phrases are defined hereinabove, with R' and R" as defined herein.

The term "N-thiocarbamate" describes an R"OC(═S)NR'— end group or a —OC(═S)NR'-linking group, as these phrases are defined hereinabove, with R' and R" as defined herein.

Thiocarbamates can be linear or cyclic, as described herein for carbamates.

The term "dithiocarbamate" as used herein encompasses S-dithiocarbamate and N-dithiocarbamate.

The term "S-dithiocarbamate" describes a —SC(═S)—NR'R" end group or a —SC(═S)NR'— linking group, as these phrases are defined hereinabove, with R' and R" as defined herein.

The term "N-dithiocarbamate" describes an R"SC(═S)NR'— end group or a —SC(═S)NR'-linking group, as these phrases are defined hereinabove, with R' and R" as defined herein.

The term "urea", which is also referred to herein as "ureido", describes a —NR'C(═O)—NR"R'" end group or a —NR'C(═O)—NR"— linking group, as these phrases are defined hereinabove, where R' and R" are as defined herein and R'" is as defined herein for R' and R".

The term "thiourea", which is also referred to herein as "thioureido", describes a —NR'—C(═S)—NR"R'" end group or a —NR'—C(═S)—NR"— linking group, with R', R" and R'" as defined herein.

The term "amide" as used herein encompasses C-amide and N-amide.

The term "C-amide" describes a —C(═O)—NR'R" end group or a —C(═O)—NR'— linking group, as these phrases are defined hereinabove, where R' and R" are as defined herein.

The term "N-amide" describes a R'C(═O)—NR"—end group or a R'C(═O)—N— linking group, as these phrases are defined hereinabove, where R' and R" are as defined herein.

An amide can be linear or cyclic. When cyclic, R' and the carbon atom are linked together to form a ring, in C-amide, and this group is also referred to as lactam. Cyclic amides can function as a linking group, for example, when an atom in the formed ring is linked to another group.

The term "guanyl" also describes a R'R"NC(═N)— end group or a —R'NC(═N)— linking group, as these phrases are defined hereinabove, where R' and R" are as defined herein.

The term "guanidine" also describes a —R'NC(═N)—NR"R'" end group or a —R'NC(═N)—NR"— linking group, as these phrases are defined hereinabove, where R', R" and R'" are as defined herein.

The term "hydrazine" describes a —NR'—NR"R'" end group or a —NR'—NR"— linking group, as these phrases are defined hereinabove, with R', R", and R'" as defined herein.

As used herein, the term "hydrazide" describes a —C(═O)—NR'—NR"R'" end group or a —C(═O)—NR'—NR"— linking group, as these phrases are defined hereinabove, where R', R" and R'" are as defined herein.

As used herein, the term "thiohydrazide" describes a —C(═S)—NR'—NR"R'" end group or a —C(═S)—NR'—NR"— linking group, as these phrases are defined hereinabove, where R', R" and R'" are as defined herein.

Herein throughout, the term "acyl" describes a —C(═O)—R group, wherein R is as described herein.

Herein throughout, the term "acyl" describes a —C(═O)—R group, with R being a substituted or unsubstituted alkyl, cycloalkyl, aryl, alkaryl, a hydrocarbon chain, or hydrogen.

According to specific embodiments, the particle comprises a detectable moiety.

According to specific embodiments, the method comprises attaching to the particle a detectable moiety.

Examples of detectable moieties that can be used in the present invention include but are not limited to radioactive isotopes, phosphorescent chemicals, chemiluminescent chemicals, fluorescent chemicals, enzymes, fluorescent polypeptides and a radioactive isotope (such as [125]iodine). The detectable moiety can be a member of a binding pair, which is identifiable via its interaction with an additional member of the binding pair, and a label which is directly visualized. In one example, the label is a fluorescent protein or an enzyme producing a colorimetric reaction.

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.]. Fluorescence detection methods which can be used to detect the fluorescent detectable moiety include, for example, fluorescence activated flow cytometry (FACS), immunofluorescence confocal microscopy, fluorescence in-situ hybridization (FISH) and fluorescence resonance energy transfer (FRET).

Further examples of detectable moieties, include those detectable by Positron Emission Tomagraphy (PET) and Magnetic Resonance Imaging (MRI), all of which are well known to those of skill in the art.

According to specific embodiments, the particle comprises a targeting moiety.

According to specific embodiments, the method comprises attaching to the particle a targeting moiety.

The term "targeting moiety", as used herein, relates to a functional group, which serves to target or direct the particle or the composition comprising same described herein to a specific cell type (e.g. cancer cell). Such targeting moieties include, but are not limited to antibodies, cell surface receptor, ligands, hormones, lipids, sugars and dextrans.

According to specific embodiments, the targeting moiety is an antibody.

Method of binding detectable or targeting moieties to a particle are known in the art and are also disclosed in the Examples section which follows and e.g. International Patent Application Publication NO. WO2018/015881, U.S. Pat. Nos. 5,171,578, 5,204,096 and 5,258,499, the contents of which are fully incorporated herein by reference.

The lipid particles disclosed herein encapsulate a nucleic acid sequence encoding a protein.

Encapsulating the nucleic acid sequence in the particle can be effected concomitant with, or following particle assembly, by methods well known in the art such as disclosed in the Examples section which follows, and also in e.g. Ramishetti et al. Adv Mater. 2020 Jan. 30:e1906128, International Patent Application publication Nos. WO2018/015881 and WO2018087753, WO2017194454 and US Patent Application Publication no. US20130245107, the contents of which are fully incorporated herein by reference.

Any suitable particle:nucleic acid sequence ratio that is efficacious is contemplated by some embodiments of the invention. According to specific embodiments, the particle: nucleic acid sequence ratios (w/w) include about 1:1 to about 50:1, about 2:1 to about 30:1, about 5:1 to about 100:1, about 10:1 to about 40:1, about 15:1 to about 25:1. According to a specific embodiment the ratio between particle: nucleic acid sequence (w/w) is 10:1.

As used herein the term "nucleic acid sequence" or "polynucleotide" refers to a single or double stranded nucleic acid sequence which is isolated and provided in the form of an RNA sequence, a complementary polynucleotide sequence (cDNA), a DNA sequence, a genomic polynucleotide sequence and/or a composite polynucleotide sequences (e.g., a combination of the above). According to a specific embodiment, the nucleic acid sequence is a messenger RNA (mRNA) sequence.

To express an exogenous protein in mammalian cells, a nucleic acid sequence encoding the protein typically comprises regulatory sequences suitable for mammalian cell expression.

Thus, for example, if the nucleic acid sequence needs to be transcribed the nucleic acid sequence is preferably ligated into a nucleic acid construct suitable for mammalian cell expression. Such a nucleic acid construct includes a promoter sequence for directing transcription of the polynucleotide sequence in the cell in a constitutive or inducible manner. The nucleic acid construct may include additional sequences, which render it suitable for replication and integration in prokaryotes, eukaryotes, or preferably both (e.g., shuttle vectors). In addition, a typical construct may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

Alternatively, or additionally, as the nucleic acid sequence needs to be translated, the nucleic acid sequence may comprise regulatory sequences such as a ribosome binding site sequence, a start codon and an in-frame stop codon.

In addition the nucleic acid sequence may contain nucleic acid sequences encoding selectable markers, reporter proteins, internal ribosome entry site (IRES) and the like.

Constructs useful in the methods according to some embodiments of the invention may be constructed using recombinant technology well known to persons skilled in the art.

The nucleic acid sequence may comprise modifications in order to e.g. increase RNA stability and minimize immunogenicity. Such modifications include 5-methoxyuridine, Pseudouridine, 5-methyl cytidine, N6-methyladenosine, 2'-O-methyl, 2'-O-methyl 3'phosphorothioate, 2'-O-methyl 3'thiophosphonoacetate, Locked nucleic acid (LNA).

The protein encoded by the nucleic acid sequence is at least 500 amino acids long.

According to specific embodiments, the protein is at least 600, at least 700, at least 800, at least 900, at least 1000, at least 1100, at least 1200, at least 1300 amino acids long, each possibility represents a separate embodiment of the present invention.

According to a specific embodiments, the protein is at least 1000 amino acids long.

The protein may be a single unit protein or a multiunit protein.

The protein may be a naturally occurring protein, a synthetic (i.e., man-made), a fusion protein or a chimeric protein.

Non-limiting examples of proteins include enzymes, transcription factors, regulatory proteins, storage proteins structural proteins, antibodies, transcription factors, hormones, growth factors, house-keeping proteins and inducible proteins.

According to specific embodiments, the protein is not an antibody.

According to specific embodiments, the protein is an enzyme. Non-limiting examples of enzymes include nuclease, protease, kinase, helicase, integrase, transferase, reductase, hydrolase, lyase, isomerase.

According to specific embodiments, the protein is a genome editing endonuclease.

Genome editing using engineered endonucleases refers to a reverse genetics method using artificially engineered nucleases to cut and create specific double-stranded breaks at a desired location(s) in the genome, which are then repaired by cellular endogenous processes such as, homology directed repair (HDS) and non-homologous end-joining (NHEJF). NHEJF directly joins the DNA ends in a double-stranded break, while HDR utilizes a homologous donor sequence as a template for regenerating the missing DNA sequence at the break point. In order to introduce specific nucleotide modifications to the genomic DNA, a donor DNA repair template containing the desired sequence must be present during HDR.

Genome editing cannot be performed using traditional restriction endonucleases since most restriction enzymes recognize a few base pairs on the DNA as their target and these sequences often will be found in many locations across the genome resulting in multiple cuts which are not limited to a desired location. To overcome this challenge and create site-specific single- or double-stranded breaks, several distinct classes of nucleases have been discovered and bioengineered to date. These include for example the meganucleases, Zinc finger nucleases (ZFNs), transcription-activator like effector nucleases (TALENs) and CRISPR/Cas system.

Meganucleases—Meganucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity. Meganucleases are found commonly in microbial species and have the unique property of having very long recognition sequences (>14 bp) thus making them naturally very specific for cutting at a desired location.

This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence.

Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8,148,098; or 8, 163,514, the contents of each are incorporated herein by reference in their entirety. Alternatively, meganucleases with site specific cutting characteristics can be obtained using commercially available technologies e.g., Precision Biosciences' Directed Nuclease Editor™ genome editing technology.

ZFNs and TALENs—Two distinct classes of engineered nucleases, zinc-finger nucleases (ZFNs) and transcription activator-like effector nucleases (TALENs), have both proven to be effective at producing targeted double-stranded breaks (Christian et al., 2010; Kim et al., 1996; Li et al., 2011; Mahfouz et al., 2011; Miller et al., 2010).

Basically, ZFNs and TALENs restriction endonuclease technology utilizes a non-specific DNA cutting enzyme which is linked to a specific DNA binding domain (either a series of zinc finger domains or TALE repeats, respectively). Typically a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is Fokl. Additionally Fokl has the advantage of requiring dimerization to have nuclease activity and this means the specificity increases dramatically as each nuclease partner recognizes a unique DNA sequence. To enhance this effect, Fokl nucleases have been engineered that can only function as heterodimers and have increased catalytic activity. The heterodimer functioning nucleases avoid the possibility of unwanted homodimer activity and thus increase specificity of the double-stranded break.

Thus, for example to target a specific site, ZFNs and TALENs are constructed as nuclease pairs, with each member of the pair designed to bind adjacent sequences at the targeted site. Upon transient expression in cells, the nucleases bind to their target sites and the Fokl domains heterodimerize to create a double-stranded break. Repair of these double-stranded breaks through the non-homologous end-joining (NHEJ) pathway often results in small deletions or small sequence insertions. Since each repair made by NHEJ is unique, the use of a single nuclease pair can produce an allelic series with a range of different deletions at the target site.

The deletions typically range anywhere from a few base pairs to a few hundred base pairs in length, but larger deletions have been successfully generated in cell culture by using two pairs of nucleases simultaneously (Carlson et al., 2012; Lee et al., 2010). In addition, when a fragment of DNA with homology to the targeted region is introduced in conjunction with the nuclease pair, the double-stranded break can be repaired via homology directed repair to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers are typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, CA).

Method for designing and obtaining TALENs are described in e.g. Reyon et al. Nature Biotechnology 2012 May; 30(5):460-5; Miller et al. Nat Biotechnol. (2011) 29:143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through www(dot)talendesign (dot)org). TALEN can also be designed and obtained commercially from e.g., Sangamo Biosciences™ (Richmond, CA).

CRISPR-Cas system (also referred to herein as "CRISPR")—Many bacteria and archea contain endogenous RNA-based adaptive immune systems that can degrade nucleic acids of invading phages and plasmids. These systems consist of clustered regularly interspaced short palindromic repeat (CRISPR) nucleotide sequences that produce RNA components and CRISPR associated (Cas) genes that encode protein components. The CRISPR RNAs (crRNAs) contain short stretches of homology to the DNA of specific viruses and plasmids and act as guides to direct Cas nucleases to degrade the complementary nucleic acids of the corresponding pathogen. Studies of the type II CRISPR/Cas system of *Streptococcus pyogenes* have shown that three components form an RNA/protein complex and together are sufficient for sequence-specific nuclease activity: the Cas nuclease, a crRNA containing 20 base pairs of homology to the target sequence, and a trans-activating crRNA (tracrRNA) (Jinek et al. Science (2012) 337: 816-821.).

It was further demonstrated that a synthetic chimeric single guide RNA (sgRNA) composed of a fusion between crRNA and tracrRNA could direct Cas to cleave DNA targets that are complementary to the crRNA in vitro. It was also demonstrated that transient expression of Cas in conjunction with synthetic gRNAs can be used to produce targeted double-stranded brakes in a variety of different species (Cho et al., 2013; Cong et al., 2013; DiCarlo et al., 2013; Hwang et al., 2013a,b; Jinek et al., 2013; Mali et al., 2013).

The CRIPSR/Cas system for genome editing contains two distinct components: a gRNA and an endonuclease e.g. Cas.

Non-limiting Examples of CRISPR nucleases include Cas9, Cas12a, Cas12b, Cas12e, Cas13a, Cas13b, Cas14, CasX and CasY. Thus, according to specific embodiments, the genome editing endonuclease is a CRISPR-associated endonuclease, e.g. Cas9, Cas12a, Cas12b, Cas12e, Cas13a, Cas13b, Cas14, CasX or CasY endonuclease.

According to specific embodiments, the genome editing endonuclease is Cas9.

The Cas9 nuclease has two functional domains: RuvC and HNH, each cutting a different DNA strand. When both of these domains are active, the Cas9 causes double strand breaks in the genomic DNA.

Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a 'double nick' CRISPR system. A double-nick can be repaired by either NHEJ or HDR depending on the desired effect on the gene target. Thus, if specificity and reduced off-target effects are crucial, using the Cas9 nickase to create a double-nick by designing two sgRNAs with target sequences in close proximity and on opposite strands of the genomic DNA would decrease off-target effect as either gRNA alone will result in nicks that will not change the genomic DNA.

According to specific embodiments, the Cas9 is the Cas9 of *Streptococcus pyogenes*.

According to specific embodiments, the nucleic acid sequence encoding Cas9 comprises chemical modifications such as 5-methoxyuridine and CleanCap.

Nucleic acids sequences encoding Cas9 are commercially available from e.g. Trilink Biotenologies Inc.

A non-limiting example of nucleic acid sequence encoding Cas9 that can be used in the present disclosure include SEQ ID NO: 4.

The sgRNA encodes a combination of the target homologous sequence (crRNA) and the endogenous bacterial RNA that links the crRNA to the Cas nuclease (tracrRNA) in a single chimeric transcript. The sgRNA/Cas complex is recruited to the target sequence by the base-pairing between the gRNA sequence and the complement genomic DNA. For successful binding of Cas, the genomic target sequence must also contain the correct Protospacer Adjacent Motif (PAM) sequence immediately following the target sequence. The binding of the sgRNA/Cas complex localizes the Cas to the genomic target sequence so that the Cas can cut both strands of the DNA causing a double-strand break. Just as with ZFNs and TALENs, the double-stranded breaks produced by CRISPR/Cas can undergo homologous recombination or NHEJ and are susceptible to specific sequence modification during DNA repair.

A significant advantage of CRISPR/Cas is that the high efficiency of this system coupled with the ability to easily create synthetic sgRNAs. This creates a system that can be readily modified to target modifications at different genomic sites and/or to target different modifications at the same site. Additionally, protocols have been established which enable simultaneous targeting of multiple genes. The majority of cells carrying the mutation present biallelic mutations in the targeted genes.

However, apparent flexibility in the base-pairing interactions between the sgRNA sequence and the genomic DNA target sequence allows imperfect matches to the target sequence to be cut by Cas.

There are a number of publically available tools to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

As described hereinabove, in order to use several genome editing systems (e.g. CRISPR/Cas system) both the genome editing endonucleases (e.g. Cas9) and a nucleic acid sequence guiding the genome editing endonuclease to a gene of interest (e.g. gRNA) should be expressed in a target cell. Thus, according to specific embodiments, the lipid particle further encapsulates a nucleic acid sequence guiding said genome editing endonuclease to a gene of interest (e.g. CRISPR system sgRNA).

According to specific embodiments, the method comprises encapsulating in the lipid particle a nucleic acid sequence guiding said genome editing endonuclease to a gene of interest (e.g. CRISPR system sgRNA).

Non-limiting examples of genes of interest include a survival gene (e.g. KRAS, BCL-2 family genes, BRAF, KPNB1, PCNA, KIF11, NIK, TOP2A), a pro-inflammatory gene (e.g. IL-1, TNFα, IFNγ, IL-12, IL-18, granulocyte-macrophage colony stimulating factor), an anti-inflammatory gene (e.g. IL4, IL-10, IL-13, IFNα, TGFβ), a cell-cycle arrest gene (e.g. p53, cyclin A, PLK1, cyclin B1, cyclin B2, CDK1, CDC20, CDC25A, CDC25C, MCMS, CKS, BIRCS, cyclin D1, cyclin D2, cyclin D3, CKAP5,) a house keeping gene, a transcription factor (e.g. Sox11, STAT1, STAT3, NFκB, FoxP3, T-bet, RORγT), a gene associated with transmission or replication of viral infections (e.g. HIV, HPV E6, HPV E7 e.g. CCR5, ACE2), a gene encoding a membrane bound receptor (e.g. Tenascin C, CD147, LGR5, CA9, TCR).

According to specific embodiments, the gene of interest is selected from the group consisting of PLK1, Cyclin D1, Sox11, STAT3, CCR5, HIV gene (e.g. gag, pol, env, tat, rev, nef, vpr, vif, vpu), T-Bet, NIK, CKAP5, LRG5, CA9, HPV E6, HPV E7, TOP2A and CDC20.

According to specific embodiments, the gene of interest is selected from the group consisting of PLK1, Cyclin D1, Sox11, STAT3, CCR5, HIV, and T-Bet.

According to a specific embodiments, the gene of interest is PLK1.

Hence, according to specific embodiments, the gRNA sequence targeting PLK1 comprises SEQ ID NO: 2 or 3.

Both cassettes (encoding the genome editing agent and the guiding nucleic acid sequence) can be on a single nucleic acid sequence or expressed from two separate nucleic acid sequences. According to a specific embodiments, the genome editing agent and the guiding nucleic acid sequence are expressed from two separate nucleic acid sequences.

As specific embodiments of the present teachings suggest use of the lipid particles described herein for delivery of the polynucleotides encoding large proteins described herein to cells, according to an aspect of the present invention, there is provided a method of producing a heterologous protein of interest, the method comprising contacting the cell with the lipid particle disclosed herein, thereby producing the heterologous protein of interest.

According to specific embodiments, the contacting is effected in-vivo.

According to other specific embodiments, the contacting is effected in-vitro or ex-vivo.

According to specific embodiments, the method comprising maintaining the cell (e.g. culturing) under conditions which allow expression of the protein of interest. Such conditions may be for example an appropriate temperature (e.g., 37° C.), atmosphere (e.g., air plus 5% $CO_2$), pH, light, medium, supplements and the like.

According to specific embodiments, the method comprising recovering the protein of interest from said cell following the contacting in accordance with standard procedures.

As the protein of interest may be a genome editing endonuclease, as described in details hereinabove, according to an aspect of the present invention, there is provided a method of producing a genetic variation in a cell, the method comprising contacting the cell with the lipid particle disclosed herein, thereby producing the genetic variation in the cell.

According to specific embodiments, the method further comprising administering the cell following the contacting to a subject having a disease in need thereof. Non-limiting examples of diseases are further described hereinbelow.

According to an additional or an alternative aspect of the present invention, there is provided a cell produced by the method.

According to an additional or an alternative aspect of the present invention, there is provided the cell produced by the method for use in treating a disease in a subject in need thereof.

The cells used according to specific embodiments of the present invention may be autologous or non-autologous; they can be syngeneic or non-syngeneic: allogeneic or xenogeneic to the subject; each possibility represents a separate embodiment of the present invention.

According to specific embodiments, the cells are autologous to the subject.

According to specific embodiments, the cells are non-autologous to the subject.

As specific embodiments suggest use of the lipid particles described herein for delivery of the polynucleotides encoding large proteins described herein to cells, specific embodiments of the present invention contemplate their use in methods of treating diseases that can benefit from expression of such proteins.

Thus, according to an aspect of the present invention, there is provided a method of treating a disease that can benefit from exogenous expression of a protein in a cell of a subject, the method comprising administering to the subject a therapeutically effective amount of the lipid particle disclosed herein, thereby treating the disease in the subject.

According to an additional or an alternative aspect of the present invention, there is provided the lipid particle disclosed herein for use in treating a disease that can benefit from exogenous expression of said protein in a cell of a subject.

According to an additional or an alternative aspect of the present invention, there is provided a method of treating a disease that can benefit from producing a genetic variation in a cell of a subject, the method comprising administering to the subject a therapeutically effective amount of the lipid particle disclosed herein, thereby treating the disease in the subject.

According to an additional or an alternative aspect of the present invention, there is provided the lipid particle disclosed herein for use in treating a disease that can benefit from producing a genetic variation in a cell of a subject.

The term "treating" or "treatment" refers to inhibiting, preventing or arresting the development of a pathology (disease, disorder or medical condition) and/or causing the reduction, remission, or regression of a pathology or a symptom of a pathology. Those of skill in the art will understand that various methodologies and assays can be used to assess the development of a pathology, and similarly, various methodologies and assays may be used to assess the reduction, remission or regression of a pathology.

As used herein, the term "subject" includes mammals, e.g., human beings at any age and of any gender. According to specific embodiments, the term "subject" refers to a subject who suffers from the pathology (disease, disorder or medical condition).

According to specific embodiments, the subject is a human.

According to specific embodiments, the disease is an inflammatory disease. Non-limiting examples of inflammatory diseases include inflammatory diseases associated with hypersensitivity, autoimmune diseases (e.g. cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases), infectious diseases (e.g. chronic infectious diseases, subacute infectious diseases, acute infectious diseases, viral diseases e.g. AIDS, coronavirus, bacterial diseases, protozoan diseases, parasitic diseases, fungal diseases, *mycoplasma* diseases and prion diseases), cancer.

According to specific embodiments, the disease is cancer.

As used herein, the term cancer encompasses both malignant and pre-malignant cancers.

According to specific embodiments, the cancer comprises malignant cancer.

Cancers which can be treated by the methods of some embodiments of the invention can be any solid or non-solid cancer and/or cancer metastasis. Examples of cancer include but are not limited to, carcinoma, lymphoma, blastoma, sarcoma, and leukemia. More particular examples of such cancers include squamous cell cancer, lung cancer (including small-cell lung cancer, non-small-cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; Burkitt lymphoma, Diffused large B cell lymphoma (DLBCL), high grade lymphoblastic NHL; high-grade small non-cleaved cell NHL; bulky disease NHL; mantle cell lymphoma; AIDS-related lymphoma; and Waldenstrom's Macroglobulinemia); T cell lymphoma, Hodgkin lymphoma, chronic lymphocytic leukemia (CLL); acute lymphoblastic leukemia (ALL); Acute myeloid leukemia (AML), Acute promyelocytic leukemia (APL), Hairy cell leukemia; chronic myeloblastic leukemia (CML); and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. The cancerous conditions amenable for treatment of the invention include metastatic cancers.

According to a specific embodiment, the cancer is glioblastoma.

According to a specific embodiment, the cancer is ovarian cancer.

According to specific embodiments, the cancer comprises pre-malignant cancer.

Pre-malignant cancers (or pre-cancers) are well characterized and known in the art (refer, for example, to Berman J J. and Henson D E., 2003. Classifying the precancers: a metadata approach. BMC Med Inform Decis Mak. 3:8). Classes of pre-malignant cancers amenable to treatment via the method of the invention include acquired small or microscopic pre-malignant cancers, acquired large lesions with nuclear atypia, precursor lesions occurring with inherited hyperplastic syndromes that progress to cancer, and acquired diffuse hyperplasias and diffuse metaplasias. Examples of small or microscopic pre-malignant cancers include HGSIL (High grade squamous intraepithelial lesion of uterine cervix), AIN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma. Examples of precursor lesions occurring with inherited hyperplastic syndromes that progress to cancer include atypical mole syndrome, C cell adenomatosis and MEA. Examples of acquired diffuse hyperplasias and diffuse metaplasias include AIDS, atypical lymphoid hyperplasia, Paget's disease of bone, post-transplant lymphoproliferative disease and ulcerative colitis.

According to specific embodiments, the disease is an infectious disease.

As used herein, the term "infection" or "infectious disease" refers to a disease induced by a pathogen. Non-limiting specific examples of pathogens include, viral pathogens, bacterial pathogens e.g., intracellular mycobacterial pathogens (such as, for example, *Mycobacterium tuberculosis*), intracellular bacterial pathogens (such as, for example, *Listeria monocytogenes*), intracellular protozoan pathogens (such as, for example, *Leishmania* and *Trypanosoma*), parasitic diseases, fungal diseases, prion diseases.

Methods of analyzing infection are well known in the art and are either based on serology, protein markers, or nucleic acid assays.

According to specific embodiments, the disease is a viral infections disease.

Non-limiting examples of viral infections include human immunodeficiency virus (HIV)-induced acquired immunodeficiency syndrome (AIDS), coronavirus, influenza, rhinoviral infection, viral meningitis, Epstein-Barr virus (EBV) infection, hepatitis A, B or C virus infection, measles, papilloma virus infection/warts, cytomegalovirus (CMV) infection, Herpes simplex virus infection, yellow fever, Ebola virus infection, rabies, etc.

According to specific embodiments, the disease is a virus-induced pneumonia. Non-limiting examples of viruses inducing pneumonia include influenza and corona viruses.

According to specific embodiments, the disease is a Coronavirus infection.

According to specific embodiments, a clinical manifestation of Coronavirus infection includes symptoms selected from the group consisting of inflammation in the lung, alveolar damage, fever, cough, shortness of breath, diarrhea, organ failure, pneumonia and/or septic shock.

As used herein, "Coronavirus" refers to enveloped positive-stranded RNA viruses that belong to the family Coronaviridae and the order Nidovirales.

Examples of Corona viruses which are contemplated herein include, but are not limited to, 229E, NL63, OC43, and HKU1 with the first two classified as antigenic group 1 and the latter two belonging to group 2, typically leading to an upper respiratory tract infection manifested by common cold symptoms.

However, Coronaviruses, which are zoonotic in origin, can evolve into a strain that can infect human beings leading to fatal illness. Thus particular examples of Coronaviruses contemplated herein are SARS-CoV, Middle East respiratory syndrome Coronavirus (MERS-CoV), and the recently identified SAR-CoV-2 [causing 2019-nCoV (also referred to as "COVID-19")].

It would be appreciated that any Coronavirus strain is contemplated herein even though SAR-CoV-2 is emphasized in a detailed manner.

According to specific embodiments, the disease is a SAR-CoV-2 infection.

According to specific embodiments, the disease is a neurodegenerative disease (e.g. Alzheimer's disease, Parkinson's disease, Huntington disease, multiple sclerosis, myasthenia gravis, amyotrophic lateral sclerosis).

According to specific embodiments, the disease is a metabolic disease (e.g. diabetes, lysosomal storage disease e.g. Gaucher's disease, metabolic syndrome, obesity).

According to specific embodiments, the disease is a genetic disease associated with a deficiency or malfunction of a protein.

Non-limiting examples of genetic diseases include cystic fibrosis, muscular dystrophy, beta thalassemia, sickle cell anemia, Huntington disease, ATTR amyloidosis.

The lipid particles or cells of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the lipid particles encapsulating the nucleic acid sequence encoding a protein or the cell contacted with the lipid particles encapsulating the nucleic acid sequence encoding a protein accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continues infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients effective to prevent, alleviate or ameliorate symptoms of a disorder (e.g., acute liver disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in-vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in-vitro, in cell cultures or experimental animals. The data obtained from these in-vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

The active agents of some embodiments of the invention can be administered to the subject as a single treatment or in combination with other established (e.g. gold standard) or experimental therapeutic regimen to treat the disease including, but not limited to analgesics, chemotherapeutic agents, radiotherapeutic agents, cytotoxic therapies (conditioning), hormonal therapy, antibodies, antibiotics, anti-inflammatory drugs, immune-suppressive drugs, and other treatment regimens (e.g., surgery) which are well known in the art.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Cell Lines—

HEK293 cells (ATCC, CRL-1573), HCT116 (ATCC, CRL-247), A549 (ATCC, CRL-185), Ovcar8 and NCI/ADR-RES (NAR) (Cohen K et al., ACS Nano 2014) were maintained in DMEM or RPMI-1640 (Gibco, Thermo-Fisher Scientific, Inc) supplemented with 10% FBS (Biological Industries, Israel), 1% L-glutmine (Gibco, Thermo-Fisher Scientific, Inc) and 1% Penicillin-Streptomycin-Nystatin (Biological Industries, Israel). 005 cells (Marumoto T et al., Nature Med 2009) were maintained in stem cell media as previously described. To generate eGFP expressing cells, HEK293 and NAR cells were stably transfected with pQCXIP-GFP/d2. All cells were routinely checked every two months for *Mycoplasma* contamination using EZ-PCR *Mycoplasma* Test Kit (Biological Industries, Israel).

RNA Sequences—

The following sgRNAs were designed and synthesized by Integrated DNA technologies sgRNA is comprised by targeting sequence of ~20 nt and a sgRNA core seq: Targeting seq GFP: GACCAGGAUGGGCACCACCC/sgRNA core (SEQ ID NO: 1); Murine PLK1: CTAGCACACCAACACGTCGT/sgRNA core (SEQ ID NO: 2); Human PLK1: AATTACATAGCTCCCGAGGT/sgRNA core (SEQ ID NO: 3). Mouse PLK1 was used for all 005 experiments, Human PLk1 was used for all HEK293, HCT116, NAR, A549 and Ovcar8 experiments. CleanCap™ Cas9 mRNA (modified, SEQ ID NO: 4) was purchased from Trilink Biotenologies Inc. To enhance RNA stability and minimize immunogenicity, Cas9 mRNA was chemically modified with 5-methoxyuridine and highly modified sgRNAs were used (IDT sgRNA XT)[10,11].

Preparation Lipid Nanoparticles (LNPs)—

The ionizable cationic lipids Dlin-MC3-DMA (MC3), lipid8 (L8), lipid1 (L1), lipid6 (L6), lipif8 (L8) and lipid10 (L10) were synthesized according to a previously described method[7,20]. Cholesterol, DSPC, PEG-DMG and DSPE-PEG were purchased from Avanti Polar Lipids Inc. One volume of lipid mixture (Ionizable lipid, DSPC, Cholesterol, DMG-PEG, and DSPE-PEG at 50:10.5:38:1.4:0.1 mol ratio) in ethanol and three volumes of Cas9 mRNA/sgRNA (1:10 molar ratio polynucleotide to ionizable lipid) in citrate buffer were injected into a microfluidic mixing device Nanoassemblr (Precision Nanosystems Inc) at a combined flow rate of 12 ml $min^{-1}$. The formed LNPs were dialysed twice against phosphate buffered saline (PBS) (pH 7.4) for 16 hours to remove ethanol. A schematic representation of the process is shown in FIG. 1A. The generated LNPs encapsulating Cas9 mRNA and the indicated sgRNA are referred to herein as cLNPs.

Size Distribution— cLNPs size distribution and -potential were determined by dynamic light scattering using a Malvern nano ZS ζ-sizer (Malvern Instruments). For size measurements, cLNPs were diluted 1:20 in PBS. All used samples showed a PDI lower than 0.2. For ζ-potential measurements, cLNPs were diluted 1:200 in double-distilled water.

Transmission Electron Microscopy—

A drop of aqueous solution containing cLNPs was placed on a carbon-coated copper grid, dried and analyzed using a JEOL 1200 EX transmission electron microscope.

ASSET LNP Incorporation and Targeted cLNP Assembly—

To incorporate ASSET into cLNPs, ASSET was incubated with LNPs for 48 hours at 4° C. (1:36, ASSET:RNA weight ratio) as previously described (Kedmi et al., Nature Nanotech 2018). Anti-human EGFR antibody (Clone Bio-Rad Laboratories, Inc. Clone: ICR10) or Rat IgG2a isotype control (BioXcell NH, USA. Clone 2A3).

RNA Quantification and Encapsulation—

To quantify the RNA in cLNPs and to determine the RNA encapsulation efficiency, Quant-iT RiboGreen RNA assay (Life Technology) by manufacturer protocol. Briefly 2 μl of cLNPs or dilutions of ribosomal RNA at known concentrations were diluted in a final volume of 100 μl of TE buffer (10 mM Tris-HCl, 20 mM EDTA) in the presence or absence of 0.5% Triton X-100 (Sigma-Aldrich) in a 96-wells fluorescent plate (Costar, Corning). The plate was incubated for 10 minutes at 40° C. to allow particles to become permeabilized before adding 99 μl of TE buffer and 1 μl of RiboGreen reagent to each well. Plates were shaken at room temperature for 5 minutes and fluorescence (excitation wavelength 485 nm, emission wavelength 528 nm) was measured using a plate reader (Biotek iindustries) according to the manufacture's protocol.

In Vitro Uptake Analysis—

For in vitro uptake analysis 20% of the total RNA content of the cLNPs was replaced with an equal amount of short Cy5.5 labeled DNA Oligo (Cy5.5 AGCTCTGTT-TACGTCCCAGC, SEQ ID NO: 5). $0.5\times10^6$ cells were incubated with 0.1-1 μg/ml of LNPs in 37° for 2 hours. Binding of the labeled cLNPs was assessed by flow cytometry (Cytoflex™ and the Cytexpert™ software, Beckman-Coulter, USA.) following three rounds of PBS wash. Analyses were effected with FlowJo™ software (FlowJo LLC, USA).

In Vitro Transfection—

Cells were counted using trypan blue (Biological industries) and $0.1\times10^6$ cells were placed in tissue culture 12-wells plates (Greiner bio-one, Germany) with 1 ml of growing medium. Mock (PBS) or cLNPs were added to the wells at RNA amounts of 0.1-2 μg and the cells were incubated with the treatments in standard culture conditions for 24-120 hours. Following, cells were washed three times and incubated in fresh culture medium. Cells were collected for flow cytometry following 72-96 hours or for cell cycle assays following 24-28 hours. For 005 cells, cLNP's were pre-incubated with 0.001 mg/ml ApoE3 (Peprotech, USA) prior their addition to the cells.

EGFP Disruption Assay—

72 hours post transfection cells were collected and the % of EGFP negative cells was evaluated using Cytoflex™ and the Cytexpert™ software (Beckman-Coulter, USA). Analyses were conducted using FlowJo software (Becton Dickinson, USA).

NGS Analysis of Gene Editing—

For sequencing analysis, genomic DNA was extracted with QuickExtract™ DNA Extraction Solution (Lucigen Inc) according to manufacturer's protocol. Amplification was performed using locus-specific primers containing universal tails to add sample-unique P5 and P7 indexes for Illumina sequencing in two rounds of PCR. Following PCR a 1×SPRI bead clean-up and library quantification by qPCR (IDT) was performed prior to sequencing. PCR amplicons were sequenced on an Illumina MiSeq instrument (v2 chemistry, 150 bp paired end reads) (Illumina, San Diego, Calif., USA). Data was analyzed using a custom-built pipeline. Data was demultiplexed (Picard tools v2.9; www(dot)github(dot)com/broadinstitute/picard); forward and reverse reads were merged into extended amplicons (flash v1.2.11)52; reads were aligned against the GRCh38 genomic reference (bwa mem v0.7.15), and were assigned to targets (bedtools tags v2.25)53. Reads with any base quality score <10 were filtered out. At each target, editing was calculated as the percentage of total reads containing an INDEL within a 8 bp window of the cut site.

Cell Cycle and Cell Viability Studies—

For cell cycle analysis, $5\times10^5$ cells were collected 48 hours post LNPs transfection. The cells were washed with ice-cold PBS and fixed with 70% ethanol for 1 hour. Following, the cells were washed twice with cold PBS and incubated for 10 minutes at 37° C. in 300 μL PBS with 15 μg/mL 2-(4-Amidinophenyl)-6-indolecarbamidine dihydrochlorid (DAPI)(Merck, KGaA, Darmstadt, Germany). Fluorescence was measured by flow cytometry. Apoptosis was evaluated by flow cytometry using AnnexinV-APC (Biolegend, Inc: 640941) and DAPI as recommended by the manufacturer. Data from at least $2\times10^4$ cells were acquired using Cytoflex™ and the Cytexpert™ software (Beckman-Coulter, USA). Analyses were effected with FlowJo™ software. For cell cycle analysis, the Dean-Jett-Fox model was applied on at least 10000 gated cells. Cell viability evaluation was effected using XTT cell proliferation kit (Biological Industries, Israel) according to manufacturer's instructions.

Animal Experiments—

All animal protocols were approved by Tel Aviv University Institutional Animal Care and Usage Committee and in accordance with current regulations and standards of the Israel Ministry of Health. All animal experiments were conducted in a double blinded fashion; the researchers were blinded to group allocation and administered treatments. Mice were randomly divided in a blinded fashion in the beginning of each experiment.

In-Vivo Glioblastoma Model—

Eight-week-old female C57BL/6JOlaHsd mice (Envigo, Rehovot, Israel) were anesthetized, positioned in a Kopf Stereotaxic Alignment System and were inoculated with $3\times10^5$ 005 glioblastoma (GBM) cells in a 1.5 μL volume using automatic syringe pump in a rate of 0.3 μl/min. Injections were made to the right frontal lobe, −1.5 mm lateral and 2 mm caudal from bregma and at a depth of 2.3 mm. Bioluminescence Imaging (IVIS-spectrum-CT Perkin Elmer Inc) was performed every 5 days following tumor cell implantation to monitor tumor growth. XenoLight D-Luciferin (122799, Perkin Elmer Inc) was injected at 15 mg/kg subcutaneously. Bioluminescence analysis was conducted using the Living Image software (Perkin Elmer Inc). Ten days post tumor inoculation mice were anesthetized, positioned in a Kopf Stereotaxic Alignment System and were injected with PBS, 0.05 mg/Kg of either cLNP encapsulating Cas9 mRNA/GFP sgRNA (sgGFP-cLNPs), LNP encapsulating Cas9 mRNA/PLK1 sgRNA (sgPLK1-cLNPs) or PBS in a 1.5 μL volume using automatic syringe pump in a rate of 0.3 μl/min. Injections were made to the right frontal lobe, −1.5 mm lateral and 2 mm caudal from bregma and at a depth of 2.3 mm. At the indicated time points, brains were harvested from sacrificed mice and processed to single cell suspensions using Neural Tissue Dissociation Kit (P) (Miltenyi Biotech, USA) and gentleMACS™ Dissociator according to manufacturer's protocol.

For in vivo tumor distribution of cLNPs, 20% of the total RNA content of the sgGFP-cLNPs was replaced with an equal amount of short Cy5.5 labeled DNA Oligo (Cy5.5 AGCTCTGTTTACGTCCCAGC, SEQ ID NO: 5), 6 hours post injection mice were sacrificed and brains were harvested. For fluorescent staining, brain coronal sections (40 μm) were cut on a microtome, and images were obtained using a confocal laser-scanning microscope.

In-Vivo Ovarian Cancer Model—

Eight-weeks-old female Hsd:Athymic Nude-Foxn1nu mice (Envigo, Rehovot, Israel) were injected with $3\times10^6$ Ovcar8-mCherry cells intraperitoneally. Fluorescence imaging (IVIS-spectrum-CT Perkin Elmer Inc) was performed weekly following tumor cell implantation to monitor tumor growth. Fluorescence analysis was conducted using the Living Image software (Perkin Elmer Inc). Ten and seventeen days post tumor inoculation mice were injected intraperitoneally with 0.75 mg/Kg of either anti EGFR-targeted sgGFP-cLNPs, Isotype control-targeted sgGFP-cLNPs, anti EGFR-targeted sgPLK1-cLNPs or Isotype control-targeted sgPLK1-cLNPs.

In Vivo Toxicity and Immunogenicity—

Ten-weeks-old female C57BL/6 mice (Envigo laboratories) were injected with 1 mg/kg sgGFP-cLNPs, intravenously. Twenty-four hours post injection blood was collected for biochemistry using Cobas-6000 instrument and complete blood count via Sysmex and Advia-120 (A.M.L, Israel). Serum was separated and stored at −80° C. prior to cytokine analysis. Cytokine analysis was effected by Pharmaseed pre-clinical CRO, Israel.

Statistical Analysis—

Statistical analysis for comparing two experimental groups was performed using two-sided Student's t-tests. In experiments with multiple groups, one or two-way ANOVA with a Tukey correction was used to calculate differences among multiple populations. Kaplan-Meier curves were used to analyze survival. A value of $P<0.05$ was considered statistically significant. Analyses were performed with Prism 7 (Graph pad Software). Differences are labelled n.s. for not significant, * for $P\leq0.05$,  for $P\leq0.01$, * for $P\leq0.001$ and **** for $P\leq0.0001$. Pre-established criteria for the removal of animals from experiment were based on animal health, behavior and well-being as required by ethical guidelines.

Example 1

Generation of Lipid Nanoparticles Encapsulating Cas9 mRNA and sgRNA

The large size of Cas9 (160 kDa, 4300b) and sgRNA (~31 kDa, 130b) is an obstacle for conventional viral and non-viral delivery into cells. To overcome the cargo limitation, lipid nanoparticles (LNPs) were designed to co-encapsulate Cas9 mRNA and sgRNA, using the gold standard DLin-MC3-DMA (hereinafter MC3) ionizable cationic lipid or an ionizable cationic lipid, lipid8 (L8), from a novel ionizable amino lipid library[7] (FIG. 1A). Cas9 mRNA, instead of plasmid DNA, was chosen to reduce exposure to the nuclease to minimize off-target gene modifications[8,9]. Specifically, the sequence of the Cas9 isolated from *Streptococcus pyogenes* (SpCas9) was used for this study. To enhance RNA stability and minimize immunogenicity, Cas9 mRNA was chemically modified with 5-methoxyuridine and highly modified sgRNAs were used (IDT sgRNA XT)[10,11]. The generated lipid nanoparticles encapsulating the Cas9 mRNA and sgRNA are referred to herein as CRISPR LNPs or cLNPs. The generated L8-based cLNPs were uniform in size, as determined by transmission electron microscopy and dynamic light scattering indicated a diameter of 79.3±1.71 nm, polydispersion index of 0.085 and -potential 7.6±0.45 mV, which was similar to that of the generated MC3-based cLNPs (FIG. 1B and Table 1 hereinbelow). Encapsulation efficiency of Cas9 mRNA and sgRNA in L8- and MC3-based LNPs was similarly high (>90%) (FIG. 1C).

TABLE 1

Characterization of the generated L1, L6, L8, L10- and MC-based cLNPs as determined by Dynamic Light Scattering and zeta sizer.

| | Size | Polydispersity index (PD1) | Z-potential |
|---|---|---|---|
| MC3-cLNPs | 89.2 ± 1.23 | 0.057 | 0.9 ± 0.29 |
| L8-cLNPs | 79.3 ± 1.71 | 0.085 | 7.6 ± 0.45 |
| L1-cLNPs | 71.2 ± 1.45 | 0.091 | 18.6 ± 0.97 |
| L6-cLNPs | 72.5 ± 2.01 | 0.024 | −3.73 ± 0.79 |
| L8-cLNPs | 80.6 ± 1.09 | 0.103 | 3.9 ± 1.01 |

Data is presented as mean ± s.d. of five independent preparations.

Example 2

L8-Based cNLPs Induce In-Vitro Gene Disruption in Transfected Cells Whereas MC3-Based cLNPs do not In the next step, cLNPs uptake into cells and their ability to induce gene disruption, was evaluated using MC3- or L8-based LNPs encapsulating Cas9 mRNA and GFP sgRNA (MC3-sgGFP-cLNPs or L8-sgGFP-cLNPs, respectively); and or L8-based LNPs encapsulating Cas9 mRNA and PLK1 sgRNA (L8-sgPLK1-cLNPs).

To evaluate LNP uptake into cells, HEK293 cells were incubated with increasing concentrations of Cy5.5-labeled MC3- or L8-based cLNPs and analyzed by flow cytometry (FIG. 1D). In-vitro gene disruption of GFP was measured by loss of GFP fluorescence after incubating MC3-sgGFP-cLNPs or L8-sgGFP-cLNPs with HEK293 cells expressing GFP (HEK/GFP cells) using flow cytometryl[12] (FIG. 1E). Although, the MC3-based cLNPs were taken up more than L8-based cLNPs by ~1.5-fold, MC3-based cLNPs failed to disrupt GFP expression at all concentrations tested (0.1-1.0 μg/ml total RNA). On the contrary, L8-based cLNPs disrupted GFP in a concentration dependent manner and GFP fluorescence was only detected in 4% of the treated cells at the highest L8-sgGFP-cLNPs concentration (FIG. 1E).

The efficiency and specificity of gene disruption was assessed by quantifying the % of gene disruption by next generation sequencing at GFP and PLK1 genomic loci after HEK/GFP cells were incubated with L8-sgGFP-cLNPs or L8-sgPLK1-cLNPs. Genomic DNA was efficiently modified at the targeted locus (94% GFP, 98% PLK1), while <0.1% was edited at the non-targeted locus (FIGS. 1F-I). The L8-sgGFP-cLNPs did not significantly affect cell viability at all tested concentrations (FIG. 5). Thus L8-based cLNPs facilitate highly efficient and specific gene editing with low toxicity.

The genome editing activity of L8-sgGFP-cLNPs was further verified in multiple cancer cell lines expressing GFP, namely 005 cells murine glioblastoma multiforme, human ovarian cancer 8 (0V8), human A549 lung adeno carcinoma, human NCI-ADR (NAR) highly drug resistant ovarian cancer, human HCT116 aggressive colorectal carcinoma (FIG. 12).

Example 3

L8-Based cNLPs Encapsulating PLK1 sgRNA Induce In-Vitro Cell Death

PLK1 is a kinase required for mitosis and lack of it leads to G2/M phase cell cycle arrest and cell death in dividing cells. Thus, the ability of L8-based LNPs encapsulating Cas9 mRNA and PLK1 sgRNA (L8-sgPLK1-cLNPs) to induce in-vitro cell death as a result of genome editing was evaluated. Treating HEK293 with 0.5 μg/ml L8-sgPLK1-cLNPs caused G2/M arrest 48 hours later, while control L8-sgGFP-cLNPs had no effect on cell cycle profile (FIGS. 1H and 6A). Cells treated with 0.5 μg/ml L8-sgPLK1-cLNPs were only 20% viable compared to untreated or L8-sgGFP-cLNPs-treated cells by XTT assay or Annexin V-DAPI staining, 96 hours post-treatment (FIGS. 1I and 6B-C). The preserved cell viability following treatment with L8-sgGFP-cLNPs (FIG. 1I) suggests that L8-based cLNPs may have low toxicity at therapeutically relevant doses.

To further explore the potential of the generated L8-based cLNPs for therapeutic genome editing, two aggressive and incurable cancer cell lines were used—the murine glioblastoma (GBM) stem cell-like 005 cell line isolated from gliomas that formed in $Tp53^{+/-}$ mice after intracerebral lentiviral transduction of activated H-Ras and Akt[13,14] and human Ovcar8 (OV8), a high grade serous ovarian adenocarcinoma cell line that is highly drug resistant and metastasizes to form ascites[15,16]. Murine GBM 005 cells possess the characteristics of almost uniformly fatal human GBM, including high invasivity, neovascularization, pleomorphism, and infiltration by immune cells[13,14] Like human ovarian cancer, which is usually diagnosed only after metastatic spread to the peritoneal cavity, intraperitoneal injection of OV8 form chemoresistant, metastatic high-grade ovarian cancer xenografts.

Incubation of GBM 005 or OV8 with L8-sgPLK1-cLNPs but not L8-sgGFP-cLNPs efficiently disrupted the PLK1 gene causing 84% and 91% genomic editing, respectively (FIGS. 2A, 2D and 7A-B). Disruption of PLK1 strongly caused G2/M cell cycle arrest measured 48 hours later (FIGS. 2B, 2E, 8A and 8C) and reduced cell viability 96 hours later by 5-fold in GBM 005 and 10-fold in OV8 as determined by XTT assay (FIGS. 2C and 2F). Similarly, staining of dying cells with annexin V and/or DAPI increased following incubation with L8-sgPLK1-cLNPs, but not L8-sgGFP-cLNPs (FIGS. 8B and 8D). Thus, L8-sgPLK1-cLNPs efficiently disrupt the targeted gene and cause cell cycle arrest and death of GBM 005 and OV8 cancer cell lines in-vitro.

Example 4

L8-Based cNLPs Induce In-Vivo Gene Disruption and can be Used for Therapeutic Genome Editing To evaluate the therapeutic potential of L8-based cLNPs for cancer, two major concerns of CRISPR/Cas9 therapeutics needed to be addressed—potential toxicity and immunogenicity. An initial study evaluated liver toxicity, blood counts, and serum inflammatory cytokines 24 hours following intravenous injection of 1 mg/kg L8-sgGFP-cLNPs into C57BL/6 mice (FIGS. 9A-C). There was no apparent clinical toxicity and no significant difference after injection in liver enzymes [alanine transaminase (ALT), aspartate aminotransferase (AST), alkaline phosphatase (ALP)], blood counts or in a panel of cytokines (IL-1β, IL-2, TNF-α, IFN-γ, IL-10). These results suggest that cLNPs are not grossly toxic or immunogenic when administered systemically at therapeutically relevant doses.

In the next step, the present inventors evaluated whether the high genome editing efficacy observed in-vitro could translate to therapeutic efficacy in-vivo using two tumor mouse models.

The first model was a GBM model. The secluded nature of the brain prevents from most drugs to enter by the systemic route. Therefore, intracranial drug administration might overcome this limitation and improve efficacyl[17,18.] To this end, GBM 005 expressing GFP, mCherry and luciferase were injected stereotactically into the mouse hippocampus (FIG. 3A). Tumors were allowed to grow for 10 days and then injected intratumorally with Cy5.5-labeled cLNPs or PBS. Mice were sacrificed 6 hours later and tumor sections visualized by fluorescence microscopy. The Cy5.5-labeled cLNPs diffused throughout the tumor (FIG. 3B).

To evaluate gene editing, 0.05 mg/kg of L8-sgGFP-cLNPs were injected sterotactically into established tumors and mice were sacrificed 7 days later and analyzed by flow cytometry for GFP expression. A single intracranial injection significantly decreased GFP fluorescence in tumor cells by ~2-fold, demonstrating in-vivo gene disruption (FIGS. 3C-D).

Following, to assess whether L8-sgPLK1-cLNPs can inhibit tumor growth, GBM 005-bearing mice were injected stereotactically once with 0.05 mg/kg of L8-sgPLK1-cLNPs or L8-sgGFP-cLNPs (FIG. 3E). A single intratumoral injection of L8-sgPLK1-cLNPs significantly reduced tumor growth compared to the control groups as quantified by live animal luciferase activity (FIGS. 3F-G) and increased median survival from 32.5 to 48 days (FIG. 3H). L8-sgGFP-cLNPs had no protective effect. 30% of L8-sgPLK1-cLNPs treated mice survived for 60 days when the experiment was terminated, while all the control mice died by 40 days. To the best of our knowledge, these findings represent the highest increased survival in these aggressive tumors following a single treatment.

The second model was an ovarian cancer model. In these settings, the inventors used L8-sgPLK1-cLNPs having an attached targeting moiety, to thereby enhance gene editing of tumor cells, reduce toxicity and editing of non-transformed cells. Specifically, as OV8 tumor cells highly express the epidermal growth factor receptor (EGFR)[21], the cLNPs were targeted to OV8 by coating them with anti-EGFR. To evaluate anti-tumor effectiveness, mice bearing OV8-mCherry malignant metastasis were injected i.p. on days 10 and 17 post tumor inoculation with 0.75 mg/kg of L8-sgPLK1-cLNPs or L8-sgGFP-cLNPs conjugated to anti-hEGFR (FIG. 4A). Tumor growth was monitored using mCherry in-vivo imaging. Treatment with anti-EGFR-targeted L8-sgPLK1-cLNPs significantly inhibited tumor growth (FIGS. 4B-C, $p<0.001$) and increased overall survival by ~80% (FIG. 4D). No significant difference was observed in the survival of control mice treated with anti-EGFR-targeted L8-sgGFP-cLNPs (FIG. 4D).

These findings highlight the therapeutic potential of targeted L8-based c-LNPs for the treatment of e.g. disseminated tumors.

Example 5

L10-Based and L1-Based cNLPs Induce In-Vitro Gene Disruption in Transfected Cells Whereas L6-Based cLNPs is Inferior In the next step several cLNPs comprising other ionizable cationic lipids from the novel ionizable amino lipid library[7], namely lipid10 (L10), lipid1(L1) and lipid6 (L6) were evaluated for their ability to induce gene disruption. To this end, L10-based, L1-based and L6-based LNPs encapsulating Cas9 mRNA and GFP sgRNA (L10-sgGFP-cLNPs, L1-sgGFP-cLNPs and L6-sgGFP-cLNPs, respectively) were generated and their effect on GFP silencing in HEK/GFP cells was evaluated, as compared to L8-sgGFP-cLNPs and MC3-sgGFP-cLNPs.

As shown in FIGS. 10-11, L10-based cLNPs demonstrated the highest encapsulation efficiency and genome editing activity; L1-based cLNPs demonstrated potent activity with lower encapsulation efficient; while L6-based cLNPs activity was inferior.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Other References are Cited Throughout the Application

1 Foo, J. & Michor, F. Evolution of acquired resistance to anti-cancer therapy. J Theor Biol 355, 10-20, doi:10.1016/j.jtbi.2014.02.025 (2014).

2 Hamis, S., Nithiarasu, P. & Powathil, G. G. What does not kill a tumour may make it stronger: <em>in silico</em> Insights into Chemotherapeutic Drug Resistance. *bioRxiv,* 230318, doi:10.1101/230318 (2018).

3 Tam, Y. K., Madden, T. D. & Hope, M. J. Pieter Cullis' quest for a lipid-based, fusogenic delivery system for nucleic acid therapeutics: success with siRNA so what about mRNA? *Journal of Drug Targeting* 24, 774-779, doi:10.1080/1061186X.2016.1221955 (2016).

4 Oberli, M. A. et al. Lipid Nanoparticle Assisted mRNA Delivery for Potent Cancer Immunotherapy. Nano Letters 17, 1326-1335, doi:10.1021/acs.nanolett.6b03329 (2017).

5 Senís, E. et al. CRISPR/Cas9-mediated genome engineering: An adeno-associated viral (AAV) vector toolbox. *Biotechnology Journal* 9, 1402-1412, doi:doi:10.1002/biot.201400046 (2014).

6 Yin, H. et al. Genome editing with Cas9 in adult mice corrects a disease mutation and phenotype. *Nature biotechnology* 32, 551-553, doi:10.1038/nbt.2884 (2014).

7 Ramishetti, S. et al. Combinatorial library of lipid nanoparticles for RNA delivery to Leukocytes. *Advanced Materials* (2019).

8 Liang, X. et al. Rapid and highly efficient mammalian cell engineering via Cas9 protein transfection. *Journal of Biotechnology* 208, 44-53 (2015).

9 Kim, S., Kim, D., Cho, S. W., Kim, J. & Kim, J.-S. Highly efficient RNA-guided genome editing in human cells via delivery of purified Cas9 ribonucleoproteins. *Genome Research* 24, 1012-1019, doi:10.1101/gr.171322.113 (2014).

10 Kauffman, K. J. et al. Efficacy and immunogenicity of unmodified and pseudouridine-modified mRNA delivered systemically with lipid nanoparticles in vivo. *Biomaterials* 109, 78-87, doi:10.1016/j.biomaterials.2016.09.006 (2016).

11 Granot, Y. & Peer, D. Delivering the right message: Challenges and opportunities in lipid nanoparticles-mediated modified mRNA therapeutics—An innate immune system standpoint. *Seminars in Immunology* 34, 68-77 (2017).

12 Fu, Y. et al. High frequency off-target mutagenesis induced by CRISPR-Cas nucleases in human cells. *Nature biotechnology* 31, 822-826, doi:10.1038/nbt.2623 (2013).

13 Marumoto, T. et al. Development of a novel mouse glioma model using lentiviral vectors. *Nature Medicine* 15, 110-116, doi:10.1038/nm.1863 (2009).

14 Friedmann-Morvinski, D. et al. Targeting NF-κB in glioblastoma: A therapeutic approach. *Sci Adv* 2, e1501292-e1501292, doi:10.1126/sciadv.1501292 (2016).

15 Hallas-Potts, A., Dawson, J. C. & Herrington, C. S. Ovarian cancer cell lines derived from non-serous carcinomas migrate and invade more aggressively than those derived from high-grade serous carcinomas. *Scientific Reports* 9, 5515, doi:10.1038/s41598-019-41941-4 (2019).

16 Mooney, R. et al. Enhanced Delivery of Oncolytic Adenovirus by Neural Stem Cells for Treatment of Metastatic Ovarian Cancer. *Mol Ther Oncolytics* 12, 79-92, doi:10.1016/j.omto.2018.12.003 (2018).

17 Gutkin, A., Cohen, Z. R. & Peer, D. Harnessing nanomedicine for therapeutic intervention in glioblastoma. *Expert Opinion on Drug Delivery* 13, 1573-1582, doi:10.1080/17425247.2016.1200557 (2016).

18 Rosenblum, D., Joshi, N., Tao, W., Karp, J. M. & Peer, D. Progress and challenges towards targeted delivery of cancer therapeutics. *Nature Communications* 9, 1410, doi:10.1038/s41467-018-03705-y (2018).

19 Veiga, N. et al. Cell specific delivery of modified mRNA expressing therapeutic proteins to leukocytes. *Nature Communications* 9, 4493, doi:10.1038/s41467-018-06936-1 (2018).

20 Kedmi, R. et al. A modular platform for targeted RNAi therapeutics. *Nature Nanotechnology* 13, 214-219, doi:10.1038/s41565-017-0043-5 (2018).

21 Kang, X., Patel, D., Ng, S. & Melchior, M. Enhanced antitumor activity with anti-epidermal growth factor receptor monoclonal antibody cetuximab in combination with carboplatin in preclinical human ovarian carcinoma models. *Molecular Cancer Therapeutics* 6, B46 (2007).

22 Wang, D. et al. Optimized CRISPR guide RNA design for two high-fidelity Cas9 variants by deep learning. *Nature Communications* 10, 4284, doi:10.1038/s41467-019-12281-8 (2019).
23 Kleinstiver, B. P. et al. Engineered CRISPR-Cas9 nucleases with altered PAM specificities. *Nature* 523, 481, doi:10.1038/nature14592 (2015).
24 Kleinstiver, B. P. et al. High-fidelity CRISPR-Cas9 nucleases with no detectable genome-wide off-target effects. *Nature* 529, 490-495, doi:10.1038/nature16526 (2016).
25 Vakulskas, C. A. et al. A high-fidelity Cas9 mutant delivered as a ribonucleoprotein complex enables efficient gene editing in human hematopoietic stem and progenitor cells. *Nature Medicine* 24, 1216-1224, doi:10.1038/s41591-018-0137-0 (2018).
26 Slaymaker, I. M. et al. Rationally engineered Cas9 nucleases with improved specificity. *Science* (*New York, N.Y.*) 351, 84-88, doi:10.1126/science.aad5227 (2016).
27 Wilbie, D., Walther, J. & Mastrobattista, E. Delivery Aspects of CRISPR/Cas for in Vivo Genome Editing. *Accounts of chemical research* 52, 1555-1564, doi:10.1021/acs.accounts.9b00106 (2019).
28 Xu, C.-F. et al. Rational designs of in vivo CRISPR-Cas delivery systems. *Advanced Drug Delivery Reviews* (2019).
29 Mout, R., Ray, M., Lee, Y.-W., Scaletti, F. & Rotello, V. M. In Vivo Delivery of CRISPR/Cas9 for Therapeutic Gene Editing: Progress and Challenges. *Bioconjug Chem* 28, 880-884, doi:10.1021/acs.bioconjchem.7b00057 (2017).
30 Hsu, P. D., Lander, E. S. & Zhang, F. Development and Applications of CRISPR-Cas9 for Genome Engineering. Cell 157, 1262-1278, doi:10.1016/j.cell.2014.05.010 (2014).
31 Long, C. et al. Postnatal genome editing partially restores dystrophin expression in a mouse model of muscular dystrophy. *Science* 351, 400 (2016).
32 Long, C. et al. Prevention of muscular dystrophy in mice by CRISPR/Cas9-mediated editing of germline DNA. *Science* 345, 1184 (2014).
33 Nelson, C. E. & Gersbach, C. A. Engineering Delivery Vehicles for Genome Editing. *Annual Review of Chemical and Biomolecular Engineering* 7, 637-662, doi:10.1146/annurev-chembioeng-080615-034711 (2016).
34 Finn, J. D. et al. A Single Administration of CRISPR/Cas9 Lipid Nanoparticles Achieves Robust and Persistent In Vivo Genome Editing. *Cell Reports* 22, 2227-2235 (2018).
35 Li, H. et al. In vivo genome editing restores haemostasis in a mouse model of haemophilia. *Nature* 475, 217, doi:10.1038/nature10177 (2011).

What is claimed is:

1. A lipid particle comprising a cationic lipid encapsulating a nucleic acid sequence, wherein said nucleic acid sequence encodes a protein having a length of at least 500 amino acids, the cationic lipid being represented by Formula I:

Formula I

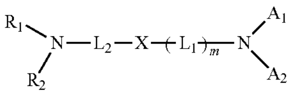

wherein:

m is 0 or 1

A1 and A2 are each independently a saturated or unsaturated linear, non-branched, alkylene chain, of at least 8 carbon atoms in length;

L1 is a first linking group which an alkylene of 1 to 4 carbon atoms in length;

X is —O—C(═O)—or —NH—C(═O);

L2 is a second linking group which is an alkylene of 1 to 4 carbon atoms in length; and R1 and R2 are each independently hydrogen, alkyl or cycloalkyl, or, alternatively, R1 and R2 form together with the nitrogen to which they are attached a heteroalicyclic ring, provided that when X is —O—C(═O)—, m is 1.

2. A method of preparing a lipid particle for delivery of a nucleic acid sequence, the method comprising encapsulating a nucleic acid sequence in a lipid particle comprising a cationic lipid represented by Formula I:

Formula I

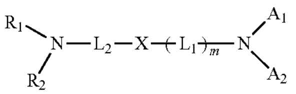

wherein:

m is 0 or 1

A1 and A2 are each independently a saturated or unsaturated linear, non-branched, alkylene chain, of at least 8 carbon atoms in length;

L1 is a first linking group which an alkylene of 1 to 4 carbon atoms in length;

X is —O—C(—O)—or —NH—C(═O);

L2 is a second linking group which is an alkylene of 1 to 4 carbon atoms in length; and R1 and R2 are each independently hydrogen, alkyl or cycloalkyl, or, alternatively, R1 and R2 form together with the nitrogen to which they are attached a heteroalicyclic ring, provided that when X is —O—C(═O)—, m is 1, wherein said nucleic acid sequence encodes a protein having a length of at least 500 amino acids.

3. The lipid particle of claim 1, wherein said lipid particle comprises a targeting moiety.

4. The method of claim 2, comprising attaching to said lipid particle a targeting moiety.

5. The lipid particle of claim 1, wherein said nucleic acid sequence is an mRNA.

6. The lipid particle of claim 1, wherein said protein is an enzyme.

7. The lipid particle of claim 6, wherein said enzyme is a genome editing endonuclease.

8. The lipid particle of claim 7, wherein said genome editing endonuclease is CRISPR-associated endonuclease.

9. The lipid particle of claim 7, wherein said lipid particle further encapsulates a nucleic acid sequence guiding said genome editing endonuclease to a gene of interest.

10. The lipid particle of claim 9, wherein said gene of interest is PLK1.

11. The lipid particle of claim 9, wherein said nucleic acid sequence guiding said genome editing endonuclease to said gene of interest is a CRISPR system gRNA.

12. The lipid particle of claim 1, wherein said particle is a nanoparticle having a size of 30-150 nm.

* * * * *

SEQUENCE LISTING

```
Sequence total quantity: 5
SEQ ID NO: 1            moltype = RNA  length = 20
FEATURE                 Location/Qualifiers
misc_feature            1..20
                        note = GFP sgRNA core
source                  1..20
                        mol_type = other RNA
                        organism = synthetic construct
SEQUENCE: 1
gaccaggatg ggcaccaccc                                              20

SEQ ID NO: 2            moltype = RNA  length = 20
FEATURE                 Location/Qualifiers
misc_feature            1..20
                        note = Murine PLK1 gRNA core
source                  1..20
                        mol_type = other RNA
                        organism = synthetic construct
SEQUENCE: 2
ctagcacacc aacacgtcgt                                              20

SEQ ID NO: 3            moltype = RNA  length = 20
FEATURE                 Location/Qualifiers
misc_feature            1..20
                        note = Human PLK1 gRNA core
source                  1..20
                        mol_type = other RNA
                        organism = synthetic construct
SEQUENCE: 3
aattacatag ctcccgaggt                                              20

SEQ ID NO: 4            moltype = RNA  length = 4245
FEATURE                 Location/Qualifiers
misc_feature            1..4245
                        note = Cas9 mRNA
source                  1..4245
                        mol_type = other RNA
                        organism = synthetic construct
SEQUENCE: 4
atggccccca agaagaagcg gaaggtgggc atccacggcg tgcccgccgc cgacaagaag  60
tacagcatcg gcctggacat cggcaccaac agcgtgggct gggccgtgat caccgacgag  120
tacaaggtgc ccagcaagaa gttcaaggtg ctgggcaaca ccgaccggca cagcatcaag  180
aagaacctga tcggcgccct gctgttcgac agcggcgaga ccgccgaggc cacccggctg  240
aagcggaccg cccggcggcg gtacacccgg cggaagaacc ggatctgcta cctgcaggag  300
atcttcagca acgagatggc caaggtggac gacagcttct tccaccggct ggaggagagc  360
```

-continued

```
ttcctggtgg aggaggacaa gaagcacgag cggcacccca tcttcggcaa catcgtggac  420
gaggtggcct accacgagaa gtaccccacc atctaccacc tgcggaagaa gctggtggac  480
agcaccgaca aggccgacct gcggctgatc tacctggccc tggcccacat gatcaagttc  540
cggggccact tcctgatcga gggcgacctg aaccccgaca acagcgacgt ggacaagctg  600
ttcatccagc tggtgcagac ctacaaccag ctgttcgagg agaaccccat caacgccagc  660
ggcgtggacg ccaaggccat cctgagcgcc cggctgagca agagccggcg gctggagaac  720
ctgatcgccc agctgcccgg cgagaagaag aacggcctgt tcggcaacct gatcgccctg  780
agcctgggcc tgacccccaa cttcaagagc aacttcgacc tggccgagga cgccaagctg  840
cagctgagca aggacaccta cgacgacgac ctggacaacc tgctggccca gatcggcgac  900
cagtacgccg acctgttcct ggccgccaag aacctgagcg acgccatcct gctgagcgac  960
atcctgcggg tgaacaccga gatcaccaag gccccccctga gcgccagcat gatcaagcgg  1020
tacgacgagc accaccagga cctgaccctg ctgaaggccc tggtgcggca gcagctgccc  1080
gagaagtaca aggagatctt cttcgaccag agcaagaacg gctacgccgg ctacatcgac  1140
ggcggcgcca gccaggagga gttctacaag ttcatcaagc ccatcctgga gaagatggac  1200
ggcaccgagg agctgctggt gaagctgaac cgggaggacc tgctgcggaa gcagcggacc  1260
ttcgacaacg gcagcatccc ccaccagatc cacctgggcg agctgcacgc catcctgcgg  1320
cggcaggagg acttctaccc cttcctgaag gacaaccggg agaagatcga gaagatcctg  1380
accttccgga tccccctacta cgtgggcccc ctggcccggg gcaacagccg gttcgcctgg  1440
atgacccgga agagcgagga gaccatcacc ccctggaact tcgaggaggt ggtggacaag  1500
ggcgccagcg cccagagctt catcgagcgg atgaccaact tcgacaagaa cctgcccaac  1560
gagaaggtgc tgcccaagca cagcctgctg tacgagtact tcaccgtgta caacgagctg  1620
accaaggtga agtacgtgac cgagggcatg cggaagcccg ccttcctgag cggcgagcag  1680
aagaaggcca tcgtggacct gctgttcaag accaaccgga aggtgaccgt gaagcagctg  1740
aaggaggact acttcaagaa gatcgagtgc ttcgacagcg tggagatcag cggcgtggag  1800
gaccggttca acgccagcct gggcacctac cacgacctgc tgaagatcat caaggacaag  1860
gacttcctgg acaacgagga gaacgaggac atcctggagg acatcgtgct gaccctgacc  1920
ctgttcgagg accgggagat gatcgaggag cggctgaaga cctacgccca cctgttcgac  1980
gacaaggtga tgaagcagct gaagcggcgg cggtacaccg gctggggccg gctgagccgg  2040
aagctgatca acggcatccg ggacaagcag agcggcaaga ccatcctgga cttcctgaag  2100
agcgacggct tcgccaaccg gaacttcatg cagctgatcc acgacgacag cctgaccttc  2160
aaggaggaca tccagaaggc ccaggtgagc ggccagggcg acagcctgca cgagcacatc  2220
gccaacctgg ccggcagccc cgccatcaag aagggcatcc tgcagaccgt gaaggtggtg  2280
gacgagctgg tgaaggtgat gggccggcac aagcccgaga acatcgtgat cgagatggcc  2340
cgggagaacc agaccaccca gaagggccag aagaacagcc gggagcggat gaagcggatc  2400
gaggagggca tcaaggagct gggcagccag atcctgaagg agcaccccgt ggagaacacc  2460
cagctgcaga acgagaagct gtacctgtac tacctgcaga acggccggga catgtacgtg  2520
gaccaggagc tggacatcaa ccggctgagc gactacgacg tggaccacat cgtgccccag  2580
agcttcctga aggacgacag catcgacaac aaggtgctga cccggagcga caagaaccgg  2640
ggcaagagcg acaacgtgcc cagcgaggag gtggtgaaga agatgaagaa ctactggcgg  2700
cagctgctga acgccaagct gatcacccag cggaagttcg acaacctgac caaggccgag  2760
cggggcggcc tgagcgagct ggacaaggcc ggcttcatca agcggcagct ggtggagacc  2820
cggcagatca ccaagcacgt ggcccagatc ctggacagcc ggatgaacac caagtacgac  2880
gagaacgaca agctgatccg ggaggtgaag gtgatcaccc tgaagagcaa gctggtgagc  2940
gacttccgga aggacttcca gttctacaag gtgcgggaga tcaacaacta ccaccacgcc  3000
cacgacgcct acctgaacgc cgtggtgggc accgccctga tcaagaagta ccccaagctg  3060
gagagcgagt tcgtgtacgg cgactacaag gtgtacgacg tgcggaagat gatcgccaag  3120
agcgagcagg agatcggcaa ggccaccgcc aagtacttct tctacagcaa catcatgaac  3180
ttcttcaaga ccgagatcac cctggccaac ggcgagatcc ggaagcggcc cctgatcgag  3240
accaacggcg agaccggcga gatcgtgtgg gacaagggcc gggacttcgc caccgtgcgg  3300
aaggtgctga gcatgcccca ggtgaacatc gtgaagaaga ccgaggtgca gaccggcggc  3360
ttcagcaagg agagcatcct gcccaagcgg aacagcgaca agctgatcgc ccggaagaag  3420
gactgggacc ccaagaagta cggcggcttc gacagcccca ccgtggccta cagcgtgctg  3480
gtggtggcca aggtggagaa gggcaagagc aagaagctga agagcgtgaa ggagctgctg  3540
ggcatcacca tcatggagcg gagcagcttc gagaagaacc ccatcgactt cctggaggcc  3600
aagggctaca aggaggtgaa gaaggacctg atcatcaagc tgcccaagta cagcctgttc  3660
gagctggaga acggccggaa gcggatgctg gccagcgccg gcgagctgca gaagggcaac  3720
gagctggccc tgcccagcaa gtacgtgaac ttcctgtacc tggccagcca ctacgagaag  3780
ctgaagggca gccccgagga caacgagcag aagcagctgt tcgtggagca gcacaagcac  3840
tacctggacg agatcatcga gcagatcagc gagttcagca agcgggtgat cctggccgac  3900
gccaacctgg acaaggtgct gagcgcctac aacaagcacc gggacaagcc catccgggag  3960
caggccgaga acatcatcca cctgttcacc ctgaccaacc tgggcgcccc cgccgccttc  4020
aagtacttcg acaccaccat cgaccggaag cggtacacca gcaccaagga ggtgctggac  4080
gccaccctga tccaccagag catcaccggc ctgtacgaga cccggatcga cctgagccag  4140
ctgggcggcg acagcggcgg caagcggccc gccgccacca agaaggccgg ccaggccaag  4200
aagaagaagg gcagctaccc ctacgacgtg cccgactacg cctga                   4245
```

```
SEQ ID NO: 5            moltype = DNA  length = 20
FEATURE                 Location/Qualifiers
misc_feature            1..20
                        note = 5' Cy5.5 conjugated
source                  1..20
                        mol_type = other DNA
                        organism = synthetic construct
SEQUENCE: 5
agctctgttt acgtcccagc                                         20
```